(12) United States Patent
Fu et al.

(10) Patent No.: US 12,673,117 B2
(45) Date of Patent: Jul. 7, 2026

(54) AAV-IDS VECTORS FOR TREATMENT OF MUCOPOLYSACCHARIDOSIS II

(71) Applicant: The University of North Carolina at Chapel Hill, Chapel Hill, NC (US)

(72) Inventors: Haiyan Fu, Durham, NC (US); Tierra Bobo, Mebane, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 470 days.

(21) Appl. No.: 18/552,549

(22) PCT Filed: Mar. 31, 2022

(86) PCT No.: PCT/US2022/022703
§ 371 (c)(1),
(2) Date: Sep. 26, 2023

(87) PCT Pub. No.: WO2022/212616
PCT Pub. Date: Oct. 6, 2022

(65) Prior Publication Data
US 2024/0366789 A1 Nov. 7, 2024

Related U.S. Application Data

(60) Provisional application No. 63/169,386, filed on Apr. 1, 2021.

(51) Int. Cl.
| | |
|---|---|
| *A61K 48/00* | (2006.01) |
| *A61P 3/00* | (2006.01) |
| *C12N 9/16* | (2006.01) |
| *C12N 15/86* | (2006.01) |
| *A61K 38/00* | (2006.01) |

(52) U.S. Cl.
CPC ............. *A61K 48/005* (2013.01); *A61P 3/00* (2018.01); *C12N 9/16* (2013.01); *C12N 15/86* (2013.01); *A61K 38/00* (2013.01); *C12N 2750/14143* (2013.01); *C12N 2830/50* (2013.01); *C12Y 301/06013* (2013.01)

(58) Field of Classification Search
CPC .... A61P 3/00; C12Y 301/06013; C12N 15/86
See application file for complete search history.

(56) References Cited

U.S. PATENT DOCUMENTS

| | | | |
|---|---|---|---|
| 2018/0071373 A1 | 3/2018 | Mcivor et al. | |
| 2019/0070311 A1 | 3/2019 | Hinderer et al. | |
| 2019/0269799 A1 | 9/2019 | Laoharawee et al. | |
| 2020/0071721 A1* | 3/2020 | Goss ...................... | A61P 25/00 |
| 2020/0246439 A1 | 8/2020 | Hinderer et al. | |
| 2021/0332383 A1* | 10/2021 | Choi ................... | A61K 9/0019 |

OTHER PUBLICATIONS

NM_000202.8, *Homo sapiens* iduronate 2-sulfatase (IDS), transcript variant 1, mRNA (Year: 2026).*
Kazusa, https://web.archive.org/web/20150720185408/http://www.kazusa.or.jp/codon/cgi-bin/showcodon.cgi?species=9606 (Year: 2015).*
Fu et al., Targeting Root Cause by Systemic scAAV9-hIDS Gene Delivery: Functional Correction and Reversal of Severe MPS II in Mice. Methods and Clinical Development (2018), 10: 327-340 (Year: 2018).*
"International Search Report and Written Opinion corresponding to International Application No. PCT/US2022/022703 mailed Jul. 13, 2022".
Cardone, Monica , et al., "Correction of Hunter syndrome in the MPSII mouse model by AAV2/8-mediated gene delivery", Human Molecular Genetics 15(7):1225-1236 (Feb. 27, 2006).
"International Preliminary Report on Patentability corresponding to International Application No. PCT/US2022/022703 mailed Oct. 12, 2023".

* cited by examiner

*Primary Examiner* — Catherine Konopka
(74) *Attorney, Agent, or Firm* — Myers Bigel, P.A.

(57) ABSTRACT

This invention relates to viral vectors for delivery of iduronate-2-sulfatase (IDS) to a subject. In some aspects the IDS sequence is optimized for expression in human cells. The invention further relates to methods of using the vector to increase secretion of IDS from a cell and for treatment and prevention of mucopolysaccharidosis II.

20 Claims, 7 Drawing Sheets

Specification includes a Sequence Listing.

AAV-IDS VECTORS FOR TREATMENT OF MUCOPOLYSACCHARIDOSIS II

STATEMENT OF PRIORITY

This application is a 35 U.S.C. § 371 national phase application of PCT Application PCT/US2022/022703 filed Mar. 31, 2022, which claims the benefit of U.S. Provisional Application Ser. No. 63/169,386 filed Apr. 1, 2021, the entire contents of each of which are incorporated by reference herein in its entirety.

STATEMENT REGARDING ELECTRONIC FILING OF A SEQUENCE LISTING

A Sequence Listing in ASCII text format, submitted under 37 C.F.R. § 1.821, entitled 5470-900WO_ST25.txt, 22,949 bytes in size, generated on Mar. 31, 2022, is filed herewith. This Sequence Listing is hereby incorporated by reference into the specification for its disclosures.

FIELD OF THE INVENTION

This invention relates to viral vectors for delivery of iduronate-2-sulfatase (IDS) to a subject. In some aspects the IDS sequence is optimized for expression in human cells. The invention further relates to methods of using the vector to increase secretion of IDS from a cell and for treatment and prevention of mucopolysaccharidosis II.

BACKGROUND OF THE INVENTION

Mucopolysaccharidosis (MPS) II, or Hunter syndrome, is a rare X-linked genetic disorder, therefore predominately a disease of males (Neufeld, E. F. & Muenzer, J. *The Mucopolysaccharidoses,* (The McGraw-Hill Companies, Inc., New York, 2014). The disease is caused by gene defects in iduronate-2-sulfatase (IDS), a lysosomal enzyme essential for the stepwise degradation of biologically important glycosaminoglycans (GAGs), heparan sulfates (HS) and dermatan sulfates (DS). While the mutations are highly heterogeneous, the lack of or reduced IDS activity results in the accumulation of undegraded or partially degraded HS and DS GAGs in cells in virtually all organs, leading to progressive multisystem disorders. Patients with MPS II typically appear normal at birth with the symptoms become apparent between 2-4 years of age. While the severity of the disease varies widely among individuals, clinically, there are 2 forms of MPS II, attenuated and severe. While both forms develop broad peripheral organ manifestations, the majority (≥70%) of MPS II patients have the severe form of the disease, with more severe somatic involvement and prominent neurological disorders that manifests as developmental delays, progressive neurodegeneration and cognitive impairment beginning by the age of 2 years. In the severe form, death generally occurs by 10-15 years of age from neurological, cardiac, or pulmonary disorders, though some with attenuated MPS II can live to adulthood.

The current standard of care for MPS II is recombinant enzyme replacement therapy (ERT)(Elaprase) delivered intravenously (IV), with demonstrated improvements in somatic symptoms in both severe and attenuated patients (Bradley et al., *Genet. Med.* 19:1187 (2017)). No treatment is currently available to treat the central nervous system (CNS) disorders in the severe form of MPS II.

Gene therapy targeting the root cause is ideal for treating MPS II, if broadly delivered to CNS and peripheral tissues, because of the potential for long-term endogenous production of recombinant enzymes. The by-stander effects of IDS enzyme allow optimal benefits without the need to transduce every cell (Neufeld et al., Ann. NY Acad. Sci. 179:580 (1971)). Among the gene delivery strategies, recombinant adeno-associated viral (rAAV) vector is an ideal tool for this application because it is safe with demonstrated long-term expression in the CNS and periphery (Foust et al., *Nat. Biotechnol.* 27:59 (2009)). The demonstrated trans-BBB-neurotropic AAV9 (Foust et al., *Nat. Biotechnol.* 27:59 (2009); Zincarelli et al., *Mol. Ther.* 16:1073 (2008); Duque et al., *Mol. Ther.* 17:1187 (2009)) has offered a great gene delivery tool for the treatment of monogenic diseases with neurological manifestations. Previously, the inventors developed a gene therapy product using rAAV9 vector to deliver the human IDS gene (hIDS) cDNA driven by the truncated miniature CMV (mCMV) promoter via systemic delivery, leading to the IND approval for a Phase I/II gene therapy clinical trial in patients with MPS II (Fu et al., Mol. Ther. Meth. Clin. Dev. 10:327 (2018).).

The present invention addresses unmet needs by providing improved therapeutic efficacy. The invention provides improved viral vectors for expression of IDS in the CNS and methods for treating or preventing MPS II.

SUMMARY OF THE INVENTION

This invention is based on the finding that the use of AAV vectors comprising a nucleic acid encoding IDS that is codon-optimized for expression in human cells provides an unexpected increase in both expression and secretion of IDS. To address unmet needs, entailing the potential of improved therapeutic efficacy, the inventors developed new second-generation self-complementary (sc) AAV9-hIDS gene therapy products by codon-optimization of hIDS and using different ubiquitous promoters. These vectors can be used advantageously for treatment of MPS II as the treatment may be more effective than previous vectors for the dual reasons of enhanced expression levels in infected cells and increased bystander effect in non-infected cells due to enhanced secretion. These advantages may provide improved efficacy at similar dosages to vectors comprising wild-type IDS sequences and/or allow effective treatment with lower doses of vector relative to vectors comprising wild-type IDS sequences.

Thus, one aspect of the invention relates to a recombinant nucleic acid comprising a sequence encoding human iduronate-2-sulfatase (IDS) that is codon-optimized for expression in human cells, wherein the recombinant nucleic acid comprises a nucleotide sequence at least 90% identical to SEQ ID NO:1.

Another aspect of the invention relates to an AAV vector genome comprising the nucleic acid of the invention, an AAV particle comprising the AAV vector genome, and a pharmaceutical composition comprising the AAV particle.

A further aspect of the invention relates to a method of producing a recombinant AAV particle comprising an AAV capsid, the method comprising: providing a cell in vitro with an AAV Cap and AAV Rep coding sequences, the AAV vector genome of the invention, and helper functions for generating a productive AAV infection; and allowing assembly of the recombinant AAV particle comprising the AAV capsid and encapsidating the AAV vector genome.

An additional aspect of the invention relates to a method of expressing IDS in a cell, comprising contacting the cell with an effective amount of an AAV particle of the invention, thereby expressing IDS in the cell.

Another aspect of the invention relates to a method of increasing secretion of IDS from a cell, comprising contacting the cell with an effective amount of the AAV particle of the invention, thereby increasing secretion of IDS from the cell relative to the secretion of IDS after contacting the cell with an AAV particle comprising a nucleic acid comprising the wild-type sequence for IDS.

A further aspect of the invention relates to a method of delivering IDS to a subject, comprising administering to the subject an effective amount of the AAV particle or the pharmaceutical formulation of the invention, thereby delivering IDS to the subject.

An additional aspect of the invention relates to a method of treating or delaying the onset of mucopolysaccharidosis II (MPS II) in a subject in need thereof, comprising administering to the subject a therapeutically effective amount of the AAV particle or the pharmaceutical formulation of the invention, thereby treating or delaying the onset of MPS II in the subject.

Another aspect of the invention relates to use of the AAV particle or the pharmaceutical formulation of the invention in a method of expressing IDS in a cell, increasing secretion of IDS from a cell, delivering IDS to a subject, or treating or delaying the onset of MPS II in a subject in need thereof These and other aspects of the invention are set forth in more detail in the description of the invention below.

DETAILED DESCRIPTION OF THE INVENTION

Figures 1, 2A, 2B, 2C, 3:
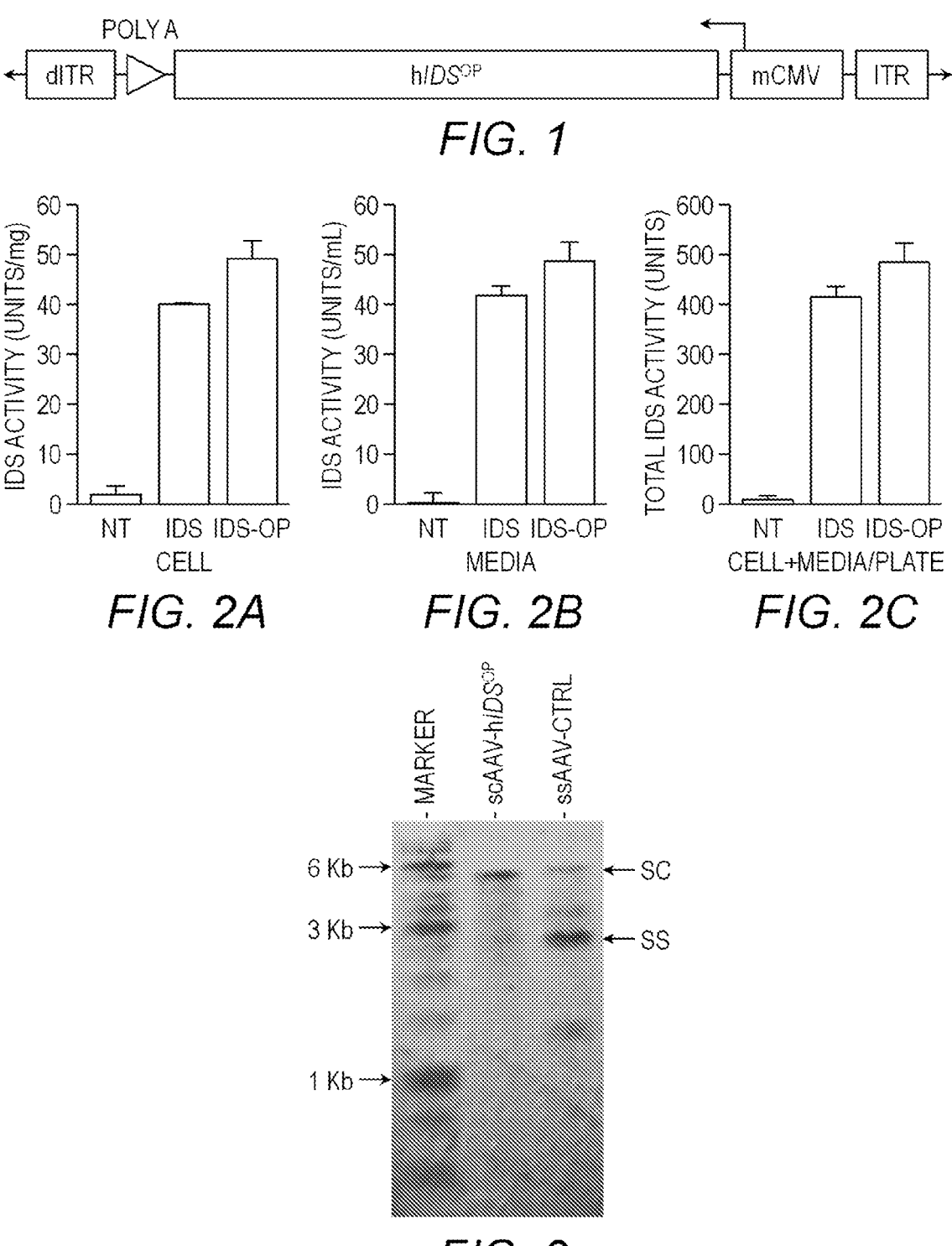
FIG. 1 shows the schematic structure of scAAV9-mCMV-hIDS$^{op}$ viral vector genome. ITR: wt AAV2 terminal repeat; dITR: AAV2 terminal repeat with deletion of terminal resolution site to force generation of self-complementary dimeric genomes; hIDS$^{op}$: codon-optimized human iduronate-2-sulfatase cDNA; mCMV: truncated human CMV promoter; Poly A: SV40 polyadenylation signal.
FIGS. 2A-2C show AAV-hIDS$^{op}$ mediated enhanced expression and secretion of rIDS in vitro. HeLa cell cultures were transfected in duplicates with 1 µg plasmid of ptrsk-mCMV-hIDS$^{op}$ or ptrsk-mCMV-hIDS. Controls were non-transfected HeLa cells. Cell lysates and media were assayed in duplicates for IDS activity at 48 h post transfection. IDS activity is expressed as units/mg protein (cells) or units/ml (media), 1 unit=1 nmol 4 MU released/hr. NT: non-transfected HeLa cells; IDS: HeLa cells transfected with ptrsk-mCMV-hIDS; IDS-op: HeLa cells transfected with ptrsk-mCMV-hIDS$^{op}$.
FIG. 3 shows generation of scAAV9-mCMV-hIDS$^{op}$ vector. HEK293 cells were co-transfected using ptrsk-mCMV-hIDS$^{op}$, pHELP and pAAV2/9 plasmids. Purified AAV9-mCMV-hIDS$^{op}$ vector product was analyzed by alkaline gel electrophoresis. sc: scAAV vector genome; ss: single-stranded control AAV vector genome.

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., *Patent In User Manual*, 99-102 (November 1990) (U.S. Patent and Trademark Office).

Except as otherwise indicated, standard methods known to those skilled in the art may be used for the construction of recombinant parvovirus and AAV (rAAV) constructs, packaging vectors expressing the parvovirus Rep and/or Cap sequences, and transiently and stably transfected packaging cells. Such techniques are known to those skilled in the art. See, e.g., SAMBROOK et al., MOLECULAR CLONING: A LABORATORY MANUAL 4th Ed. (Cold Spring Harbor, NY, 2012); AUSUBEL et al., CURRENT PROTOCOLS IN MOLECULAR BIOLOGY (Green Publishing Associates, Inc. and John Wiley & Sons, Inc., New York).

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

Definitions

The following terms are used in the description herein and the appended claims.

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps and those that do not materially affect the basic and novel characteristic(s) of the claimed invention (e.g., rAAV replication). Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in enzymatic activity of at least about 50% or more as compared to the activity of a polypeptide consisting of the recited sequence.

The term "parvovirus" as used herein encompasses the family Parvoviridae, including autonomously-replicating parvoviruses and dependoviruses. The autonomous parvoviruses include members of the genera *Parvovirus, Erythrovirus, Densovirus, Iteravirus,* and *Contravirus.* Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al., VIROLOGY, volume 2, chapter 69 (4th ed., Lippincott-Raven Publishers).

The genus *Dependovirus* contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al., VIROLOGY, volume 2, chapter 69 (4th ed., Lippincott-Raven Publishers); and Table 1.

TABLE 1

| AAV Serotypes/ Isolates | GenBank Accession Number | AAV Serotypes/ Isolates | GenBank Accession Number | AAV Serotypes/ Isolates | GenBank Accession Number |
|---|---|---|---|---|---|
| Clonal Isolates | | Hu S17 | AY695376 | Cy3 | AY243019 |
| Avian AAV ATCC VR-865 | AY186198, AY629583, NC_004828 | Hu T88 Hu T71 Hu T70 | AY695375 AY695374 AY695373 | Cy5 Rh13 Clade E | AY243017 AY243013 |
| Avian AAV strain DA-1 Bovine AAV | NC_006263, AY629583 NC_005889, AY388617 | Hu T40 Hu T32 Hu T17 Hu LG15 | AY695372 AY695371 AY695370 AY695377 | Rh38 Hu66 Hu42 Hu67 | AY530558 AY530626 AY530605 AY530627 |
| AAV4 | NC_001829 | Clade C | | Hu40 | AY530603 |
| AAV5 | AY18065, AF085716 | AAV 3 AAV 3B | NC_001729 NC_001863 | Hu41 Hu37 | AY530604 AY530600 |
| Rh34 | AY243001 | Hu9 | AY530629 | Rh40 | AY530559 |
| Rh33 | AY243002 | Hu10 | AY530576 | Rh2 | AY243007 |
| Rh32 | AY243003 | Hu11 | AY530577 | Bb1 | AY243023 |
| AAV10 | AY631965 | Hu53 | AY530615 | Bb2 | AY243022 |
| AAV11 | AY631966 | Hu55 | AY530617 | Rh10 | AY243015 |
| AAV12 | DQ813647 | Hu54 | AY530616 | Hu17 | AY530582 |
| AAV13 | EU285562 | Hu7 | AY530628 | Hu6 | AY530621 |

TABLE 1-continued

| AAV Serotypes/ Isolates | GenBank Accession Number | AAV Serotypes/ Isolates | GenBank Accession Number | AAV Serotypes/ Isolates | GenBank Accession Number |
|---|---|---|---|---|---|
| Clade A | | Hu18 | AY530583 | Rh25 | AY530557 |
| | | | | | |
| AAV1 | NC_002077, | Hu15 | AY530580 | Pi2 | AY530554 |
| | AF063497 | Hu16 | AY530581 | Pi1 | AY530553 |
| AAV6 | NC_001862 | Hu25 | AY530591 | Pi3 | AY530555 |
| Hu.48 | AY530611 | Hu60 | AY530622 | Rh57 | AY530569 |
| Hu 43 | AY530606 | Ch5 | AY243021 | Rh50 | AY530563 |
| Hu 44 | AY530607 | Hu3 | AY530595 | Rh49 | AY530562 |
| Hu 46 | AY530609 | Hu1 | AY530575 | Hu39 | AY530601 |
| Clade B | | Hu4 | AY530602 | Rh58 | AY530570 |
| | | | | | |
| Hu19 | AY530584 | Hu2 | AY530585 | Rh61 | AY530572 |
| Hu20 | AY530586 | Hu61 | AY530623 | Rh52 | AY530565 |
| Hu23 | AY530589 | Clade D | | Rh53 | AY530566 |
| | | | | | |
| Hu22 | AY530588 | Rh62 | AY530573 | Rh51 | AY530564 |
| Hu24 | AY530590 | Rh48 | AY530561 | Rh64 | AY530574 |
| Hu21 | AY530587 | Rh54 | AY530567 | Rh43 | AY530560 |
| Hu27 | AY530592 | Rh55 | AY530568 | AAV8 | AF513852 |
| Hu28 | AY530593 | Cy2 | AY243020 | Rh8 | AY242997 |
| Hu29 | AY530594 | AAV7 | AF513851 | Rh1 | AY530556 |
| Hu63 | AY530624 | Rh35 | AY243000 | Clade F | |
| | | | | | |
| Hu64 | AY530625 | Rh37 | AY242998 | AAV9 (Hu14) | AY530579 |
| Hu13 | AY530578 | Rh36 | AY242999 | Hu31 | AY530596 |
| Hu56 | AY530618 | Cy6 | AY243016 | Hu32 | AY530597 |
| Hu57 | AY530619 | Cy4 | AY243018 | | |
| Hu49 | AY530612 | | | | |
| Hu58 | AY530620 | | | | |
| Hu34 | AY530598 | | | | |
| Hu35 | AY530599 | | | | |
| AAV2 | NC_001401 | | | | |
| Hu45 | AY530608 | | | | |
| Hu47 | AY530610 | | | | |
| Hu51 | AY530613 | | | | |
| Hu52 | AY530614 | | | | |
| Hu T41 | AY695378 | | | | |

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al., VIROL-OGY, volume 2, chapter 69 (4th ed., Lippincott-Raven Publishers). A number of relatively new AAV serotypes and clades have been identified (See, e.g., Gao et al., (2004) *J. Virol.* 78:6381; Moris et al., (2004) *Virol.* 33-:375; and Table 1).

The parvovirus vectors, particles, and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) *J. Virol.* 73: 939; Chiorini et al., (1997) *J. Virol.* 71:6823; Chiorini et al., (1999) *J. Virol.* 73:1309; Gao et al., (2002) *Proc. Nat. Acad. Sci. USA* 99:11854; Moris et al., (2004) *Virol.* 33-:375-383; Mori et al., (2004) *Virol.* 330: 375; Muramatsu et al., (1996) *Virol.* 221:208; Ruffing et al., (1994) *J. Gen. Virol.* 75:3385; Rutledge et al., (1998) *J. Virol.* 72:309; Schmidt et al., (2008) *J. Virol.* 82:8911; Shade et al., (1986) *J. Virol.* 58:921; Srivastava et al., (1983) *J. Virol.* 45:555; Xiao et al., (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, PA (incorporated herein in its entirety).

The term "tropism" as used herein refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, "transduction" of a cell by parvovirus or AAV refers to parvovirus/AAV-mediated transfer of genetic material into the cell. See, e.g., FIELDS et al., VIROLOGY, volume 2, chapter 69 (3d ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be. As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotides), and can be either single or double stranded DNA sequences.

The term "codon-optimized," as used herein, refers to a gene coding sequence that has been optimized to increase expression by substituting one or more codons normally present in a coding sequence (for example, in a wildtype sequence, including, e.g., a coding sequence for NAGLU) with a codon for the same (synonymous) amino acid. In this manner, the protein encoded by the gene is identical, but the underlying nucleobase sequence of the gene or corresponding mRNA is different. In some embodiments, the optimization substitutes one or more rare codons (that is, codons for tRNA that occur relatively infrequently in cells from a particular species) with synonymous codons that occur more frequently to improve the efficiency of translation. For example, in human codon-optimization one or more codons in a coding sequence are replaced by codons that occur more frequently in human cells for the same amino acid. Codon optimization can also increase gene expression through other mechanisms that can improve efficiency of transcription and/or translation. Strategies include, without limitation, increasing total GC content (that is, the percent of guanines and cytosines in the entire coding sequence), decreasing CpG content (that is, the number of CG or GC dinucleotides in the coding sequence), removing cryptic splice donor or acceptor sites, and/or adding or removing ribosomal entry sites, such as Kozak sequences. Desirably, a codon-optimized gene exhibits improved protein expression, for example, the protein encoded thereby is expressed at a detectably greater level in a cell compared with the level of expression of the protein provided by the wildtype gene in an otherwise similar cell.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., Nucl. Acid Res. 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351 (1987); the method is similar to that described by Higgins & Sharp, CABIOS 5:151 (1989).

Another example of a useful algorithm is the BLAST algorithm, described in Altschul et al., J. Mol. Biol. 215:403 (1990) and Karlin et al., Proc. Natl. Acad. Sci. USA 90:5873 (1993). A particularly useful BLAST program is the WU-BLAST-2 program which was obtained from Altschul et al., Meth. Enzymol., 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., Nucleic Acids Res. 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify." (or grammatical equivalents) a virus vector, it is meant that the virus vector is at least partially separated from at least some of the other components in the starting material.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. In some embodiments, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone or a plasmid.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged.

A "rAAV vector genome" or "rAAV genome" is an AAV genome (i.e., vDNA) that comprises one or more heterologous nucleic acid sequences. rAAV vectors generally require only the 145 base ITR in cis to generate virus. All other viral sequences are dispensable and may be supplied in trans (Muzyczka (1992) Curr. Topics Microbiol. Immunol. 158: 97). Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al., VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, persistence, and/or provirus rescue, and the like.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) *Mol. Therapy* 2:619.

Further, the viral capsid or genomic elements can contain other modifications, including insertions, deletions and/or substitutions.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40) proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see. e.g., Urabe et al., (2002) *Human Gene Therapy* 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

Parvovirus Vectors Expressing IDS

The present invention provides parvovirus vectors, e.g., AAV vectors, that comprise a nucleotide sequence encoding IDS that is codon-optimized for expression in human cells and are capable of provided enhanced expression and secretion of IDS from cells infected with the vector.

One aspect of the invention relates to a recombinant nucleic acid comprising, consisting essentially of, or consisting of a nucleotide sequence encoding human iduronate-2-sulfatase (IDS) that is codon-optimized for expression in human cells. In certain embodiments, the nucleic acid is a non-naturally occurring sequence. In some embodiments, the nucleic acid comprises, consists essentially of, or consists of a nucleotide sequence that is at least 90% identical to SEQ ID NO:1, e.g., at least 91%, 92%, 93%, 94%, 95%, 96%, 97%, 98%, or 99% identical to SEQ ID NO:1. In some embodiments, the nucleic acid comprises, consists essentially of, or consists of the nucleotide sequence of SEQ ID NO:1. In some embodiments, the nucleic acid comprises at least 10 contiguous nucleotides of SEQ ID NO:1, e.g., at least 10, 25, 50, 100, 200, 300, 400, 500, 600, 700, 800, 900, 1000, 1100, 1200, 1300, 1400, 1500, 1600, 1700, 1800, 1900, 2000, 2100 or more.

Methods of codon optimizing a nucleotide sequence to maximize expression in an organism are well known in the art and can be carried out using software available to the public. The wild-type sequence of human IDS is known in the art and shown in SEQ ID NO:2.

The invention also provides a viral vector genome comprising the IDS nucleic acid of the invention. The viral vector genome may be a parvovirus vector genome, e.g., an AAV vector genome. In some embodiments, the AAV vector genome is a self-complementary AAV vector genome. The viral vector genome may further comprise a promoter operably linked to the IDS nucleic acid. In some embodiments, the promoter may be a constitutive promoter, e.g., the CBA promoter or the CMV promoter. In other embodiments, the promoter may be a tissue-specific or preferred promoter.

Examples include, without limitation, the vector product scAAV-mCMV-hIDS$^{op}$, comprising, consisting essentially of, or consisting of SEQ ID NO:3 or a sequence at least 90% identical to SEQ ID NO:3, e.g., at least 91%, 92%, 93%, 94%, 95%, 96%, 97%, 98%, or 99% identical to SEQ ID NO:3.

The invention further provides a cell in vitro comprising the AAV vector genome of the invention, e.g., stably incorporated into the genome of the cell. The invention further provides a recombinant parvovirus particle (e.g., a recombinant AAV particle, e.g., an AAV9) particle) comprising the viral vector genome of the invention. The AAV particle may be any serotype, e.g., a serotype disclosed in Table 1. Viral vectors and viral particles are discussed further below.

In some embodiments, the viral vector genome is encoded by a plasmid. Examples include, without limitation, a plasmid encoding ptrsk-mCMV-hIDS$^{op}$ for producing the vector product scAAV-mCMV-hIDS$^{op}$, comprising, consisting essentially of, or consisting of SEQ ID NO:4 or a sequence at least 90% identical to SEQ ID NO:4, e.g., at least 91%, 92%, 93%, 94%, 95%, 96%, 97%, 98%, or 99% identical to SEQ ID NO:4.

Methods of Producing Virus Vectors

The present invention further provides methods of producing virus vectors. In one particular embodiment, the present invention provides a method of producing a recombinant parvovirus particle, comprising providing to a cell permissive for parvovirus replication: (a) a recombinant parvovirus template comprising (i) the nucleic acid encoding IDS of the invention, and (ii) a parvovirus ITR; (b) a polynucleotide comprising Rep and Cap coding sequences; under conditions sufficient for the replication and packaging of the recombinant parvovirus template; whereby recombinant parvovirus particles are produced in the cell. Conditions sufficient for the replication and packaging of the recombinant parvovirus template can be, e.g., the presence of AAV sequences sufficient for replication of the parvovirus template and encapsidation into parvovirus capsids (e.g., parvovirus rep sequences and parvovirus cap sequences) and helper sequences from adenovirus and/or herpesvirus. In particular embodiments, the parvovirus template comprises two parvovirus ITR sequences, which are located 5' and 3' to the heterologous nucleic acid sequence, although they need not be directly contiguous thereto.

In some embodiments, the recombinant parvovirus template comprises an ITR that is not resolved by Rep to make duplexed AAV vectors as described in international patent publication WO 01/92551.

The parvovirus template and parvovirus rep and cap sequences are provided under conditions such that virus vector comprising the parvovirus template packaged within the parvovirus capsid is produced in the cell. The method can further comprise the step of collecting the virus vector from the cell. The virus vector can be collected from the medium and/or by lysing the cells.

The cell can be a cell that is permissive for parvoviral viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other E1a trans-complementing cells.

The parvovirus replication and capsid sequences may be provided by any method known in the art. Current protocols typically express the parvovirus rep/cap genes on a single plasmid. The parvovirus replication and packaging sequences need not be provided together, although it may be convenient to do so. The parvovirus rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the parvovirus cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158:67).

As a further alternative, the rep/cap sequences may be stably incorporated into a cell.

Typically the parvovirus rep/cap sequences will not be flanked by the TRs, to prevent rescue and/or packaging of these sequences.

The parvovirus template can be provided to the cell using any method known in the art. For example, the template can be supplied by a non-viral (e.g., plasmid) or viral vector. In particular embodiments, the parvovirus template is supplied by a herpesvirus or adenovirus vector (e.g., inserted into the E1a or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the parvovirus template is provided by a replicating rAAV virus. In still other embodiments, an AAV provirus comprising the parvovirus template is stably integrated into the chromosome of the cell.

To enhance virus titers, helper virus functions (e.g., adenovirus or herpesvirus) that promote a productive parvovirus infection can be provided to the cell. Helper virus sequences necessary for parvovirus replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient parvovirus production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the parvovirus replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the parvovirus rep/cap sequences and the adenovirus helper sequences are supplied by a single adenovirus helper vector. This vector can further comprise the parvovirus template. The parvovirus rep/cap sequences and/or the parvovirus template can be inserted into a deleted region (e.g., the E1a or E3 regions) of the adenovirus.

In a further embodiment, the parvovirus rep/cap sequences and the adenovirus helper sequences are supplied by a single adenovirus helper vector. According to this embodiment, the parvovirus template can be provided as a plasmid template.

In another illustrative embodiment, the parvovirus rep/cap sequences and adenovirus helper sequences are provided by a single adenovirus helper vector, and the parvovirus template is integrated into the cell as a provirus. Alternatively, the parvovirus template is provided by an EBV vector that is maintained within the cell as an extrachromosomal element (e.g., as an EBV based nuclear episome).

In a further exemplary embodiment, the parvovirus rep/cap sequences and adenovirus helper sequences are provided by a single adenovirus helper. The parvovirus template can be provided as a separate replicating viral vector. For example, the parvovirus template can be provided by a parvovirus particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The parvovirus rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the parvovirus rep/cap sequences are generally not flanked by ITRs so that these sequences are not packaged into the parvovirus virions.

Zhang et al., ((2001) *Gene Ther.* 18:704-12) describe a chimeric helper comprising both adenovirus and the AAV rep and cap genes.

Herpesvirus may also be used as a helper virus in parvovirus packaging methods. Hybrid herpesviruses encoding the parvovirus Rep protein(s) may advantageously facilitate scalable parvovirus vector production schemes. A hybrid herpes simplex virus type I (HSV-1) vector expressing the AAV-2 rep and cap genes has been described (Conway et al., (1999) *Gene Ther.* 6:986 and WO 00/17377.

As a further alternative, the virus vectors of the invention can be produced in insect cells using baculovirus vectors to deliver the rep/cap genes and parvovirus template as described, for example, by Urabe et al., (2002) *Human Gene Ther.* 13:1935-43.

Parvovirus vector stocks free of contaminating helper virus may be obtained by any method known in the art. For example, parvovirus and helper virus may be readily differentiated based on size. Parvovirus may also be separated away from helper virus based on affinity for a heparin substrate (Zolotukhin et al., (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of parvovirus. Adenovirus mutants defective for late gene expression are known in the art (e.g., ts100K and ts149 adenovirus mutants).

Recombinant Virus Vectors

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells. In particular, the virus vectors of the present invention are useful for the delivery of a nucleic acid encoding IDS to a subject.

It will be understood by those skilled in the art that the nucleic acid encoding IDS can be operably associated with appropriate control sequences. For example, the nucleic acid can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the IDS nucleic acid sequence. The promoter/enhancer element is generally chosen so that it functions in the target cell(s) of interest. Further, in particular embodiments the promoter/enhancer element is a mammalian promoter/enhancer element. In particular embodiments, the promoter/enhancer element functions in all cells so that IDS is expressed systemically. The promoter/enhancer element may be constitutive or inducible.

Inducible expression control elements are typically advantageous in those applications in which it is desirable to provide regulation over expression of the nucleic acid sequence. Inducible promoters/enhancer elements for gene delivery can be tissue-specific or -preferred promoter/enhancer elements, and include neuron specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the nucleic acid sequence is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors of the invention can be parvovirus vectors, e.g., AAV vectors. The AAV vectors may be any AAV serotype. In some embodiments, the AAV vector is an AAV2, AAV8, or AAV9 vector. In some embodiments, the AAV vector is a hybrid vector, e.g., one having a capsid protein from one serotype and a genome from another serotype or one having a synthetic capsid protein. In certain embodiments, the vector comprises a hybrid capsid with an altered tropism. In one example the hybrid capsid comprising a glycan binding site (e.g., a galactose binding site) from one serotype (e.g., AAV9) in a capsid sequence from another serotype (e.g., AAV8) (see, e.g., WO 2014/144229, incorporated by reference herein in its entirety).

The virus vectors according to the present invention provide a means for delivering IDS nucleic acids into a broad range of cells, including dividing and non-dividing cells. The virus vectors can be employed to deliver the nucleic acid to a cell in vitro, e.g., to produce a polypeptide in vitro or for ex vivo gene therapy. The virus vectors are additionally useful in a method of delivering the nucleic acid to a subject in need thereof, e.g., to express IDS. In this manner, the polypeptide can be produced in vivo in the subject. The subject can be in need of the polypeptide because the subject has a deficiency of the polypeptide. Further, the method can be practiced because the production of the polypeptide in the subject may impart some beneficial effect.

The virus vectors can also be used to produce IDS in cultured cells or in a subject (e.g., using the subject as a bioreactor to produce the polypeptide or to observe the effects of the polypeptide on the subject, for example, in connection with screening methods).

The virus vectors of the present invention can be employed to deliver a nucleic acid encoding IDS to treat and/or prevent any disease state for which it is beneficial to deliver IDS, e.g., MPS II.

Virus vectors according to the instant invention find use in diagnostic and screening methods, whereby the IDS nucleic acid is transiently or stably expressed in a cell culture system, in an organ or organ culture, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

Alternatively, the virus vector may be administered to a cell ex vivo, and the altered cell is administered to the subject. The virus vector comprising the IDS nucleic acid is introduced into the cell, and the cell is administered to the subject, where the nucleic acid can be expressed.

Subjects, Pharmaceutical Formulations, and Modes of Administration

Virus vectors and capsids according to the present invention find use in both veterinary and medical applications. Suitable subjects include both avians and mammals. The term "avian" as used herein includes, but is not limited to, chickens, ducks, geese, quail, turkey's, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults.

In particular embodiments, the present invention provides a pharmaceutical composition comprising a virus vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

The cell(s) into which the virus vector is introduced can be of any type. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see. e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

A further aspect of the invention is a method of administering the virus vector to subjects. Administration of the virus vectors according to the present invention to a human subject or an animal in need thereof can be by any means known in the art. Optionally, the virus vector is delivered in a treatment effective or prevention effective dose in a pharmaceutically acceptable carrier.

Dosages of the virus vector to be administered to a subject depend upon the mode of administration, the disease or condition to be treated and/or prevented, the individual subject's condition, the particular virus vector, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$ transducing units, optionally about $10^8$ to about $10^{15}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include systemic administration, e.g., intravenous administration. The vector may also be delivered to the CNS, e.g., by intrathecal, intracerebral, intraventricular, intranasal, intra-aural, intraocular, or peri-ocular delivery administration). In some embodiments, the vector may be delivered both systemically and to the CNS.

Delivery to a target tissue can also be achieved by delivering a depot comprising the virus vector. In representative embodiments, a depot comprising the virus vector is implanted into the tissue or the tissue can be contacted with a film or other matrix comprising the virus vector. Such implantable matrices or substrates are described in U.S. Pat. No. 7,201,898.

In particular embodiments, a virus vector according to the present invention is administered systematically, e.g., intravenously, to treat, delay the onset of and/or prevent symptoms associated with MPS II.

Thus, as one aspect, the invention further encompasses a method of delivering IDS to a subject, comprising administering to the subject an effective amount of an AAV particle that expresses IDS, thereby delivering IDS to the subject.

In another aspect, the invention further encompasses a method of treating, delaying the onset of, and/or preventing MPS II or one or more symptoms associated with MPS II in a subject in need thereof, comprising administering to the subject a therapeutically effective amount of an AAV particle that expresses IDS, thereby treating, delaying the onset of, and/or preventing MPS II or one or more symptoms associated with MPS II in the subject.

In the methods of the invention, the subject may be one has been diagnosed with MPS II or is suspected of having MPS II. In certain embodiments, the subject is an infant or child, e.g., less than 18 years old, e.g., less than 18, 17, 16, 15, 14, 13, 12, 11, 10, 9, 8, 7, 6, or 5 years old. In some embodiments, the subject has not developed symptoms of MPS II.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local manner, for example, in a depot or sustained-release formulation. Further, the virus vector and/or virus capsid can be delivered adhered to a surgically implantable matrix (e.g., as described in U.S. Patent Publication No. 2004-0013645).

Having described the present invention, the same will be explained in greater detail in the following examples, which are included herein for illustration purposes only, and which are not intended to be limiting to the invention.

EXAMPLE 1

Development of Improved rAAV-hIDS Vectors rAAV vector product: The inventors have previously established that delivery of wild-type hIDS by AAV vector (first generation vector) is effective to treat MPS II (Fu et al., Mol. Ther. Meth. Clin. Dev. 10:327 (2018), incorporated by reference herein in its entirety). To develop more effective gene therapy products for treating MPS II, a scAAV vector plasmid, ptrsk-mCMV-hIDS$^{op}$, was constructed to produce the second generation scAAV vector, scAAV-mCMV-hIDS$^{op}$. The second generation scAAV vector genome contains only minimal elements required for transgene expression, including AAV2 terminal repeats, codon-optimized hIDS cDNA (hIDS$^{op}$) and SV40 Poly A signal, controlled by a truncated miniature CMV promoter (mCMV). FIG. 1 illustrates the structure of the scAAV-mCMV-hIDS$^{op}$ viral vector genome.

Codon-modification enhanced secretion of rIDS: To assess the impacts of codon-optimization on the transgene product, the scAAV-mCMV-hIDS$^{op}$ construct (ptrsk-mCMV-hIDS$^{op}$) was tested in vitro in Hela cells by transfection, using the first generation scAAV-mCMV-hIDS vector construct (ptrsk-mCMV-hIDS) as control. ptrsk-mCMV-hIDS$^{op}$ resulted in significant increases of IDS activity in both cell lysates (FIG. 2A) and the media (FIG. 2B), compared to ptrsk-mCMV-hIDS. Further, total combined NAGLU activity levels (cell lysates+media/transfection plate) were significantly higher in samples transfected with ptrsk-mCMV-hIDS$^{op}$, than in samples transfected with the control ptrsk-mCMV-hIDS (FIG. 2C). These data indicate that the codon-optimization significantly increased the expression of rIDS, more importantly, with significantly enhanced secretion of the recombinant enzyme. Interestingly, 3 other codon-optimized IDS sequences (SEQ ID NOS:5-7) were prepared and tested that did not exhibit enhanced expression or secretion. It is believed that the codon-optimized rAAV-mCMV-hIDS$^{op}$ vector has added therapeutic benefits for treating MPS II over the first generation product scAAV-mCMV-hIDS), by improved expression and enhanced by-stander effects of rIDS.

ptrsk-mCMV-hIDS$^{op}$ generates self-complementary AAV viral vector: To determine whether the new ptrsk-mCMV-hIDS$^{op}$ plasmid construct generated scAAV vector, 3-plasmid-transient-cotransfection was performed in HEK293 cells to produce AAV9-mCMV-hIDS viral vector. The purified vector product was analyzed by alkaline-gel electrophoresis. The control was an AAV vector product from a scAAV plasmid that generates only single-stranded AAV vector. The results showed that the new vector plasmid, ptrsk-mCMV-hIDS$^{op}$ generated scAAV vector (FIG. 3).

Figure 4A:
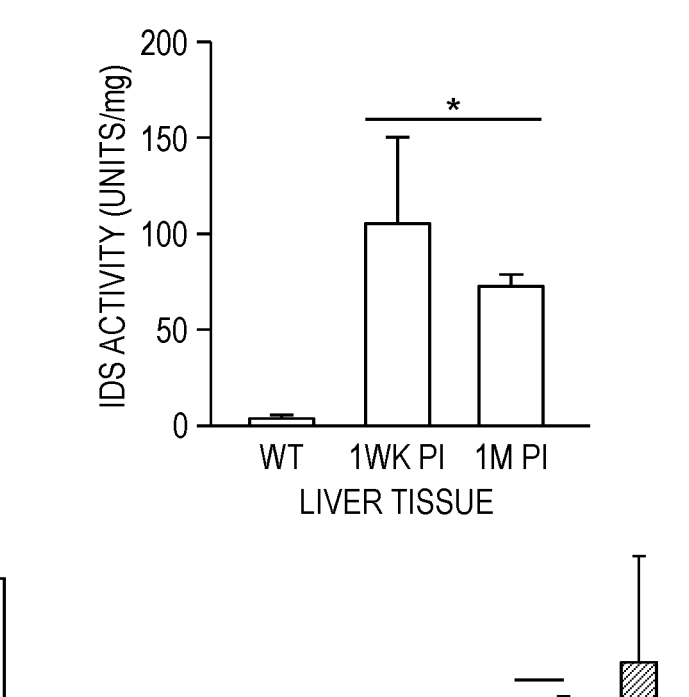
FIGS. 4A-4B show rapid restoration of IDS activity and clearance of lysosomal GAG storage in the CNS and peripheral tissues in MPS II mice following systemic scAAV9-hIDS$^{op}$ gene delivery. MPS II mice were treated at age 1 m with an IV injection of $2 \times 10^{13}$ vg/kg scAAV9)-mCMV-hIDS$^{op}$ vector. At 1 wk or 1 m pi, tissues (n=4/group) were assayed for IDS activity (a) and GAG contents (b). IDS activity is expressed as units/mg protein, 1 unit=1 nmol 4 MU released/hr. GAG content is expressed as µg/mg wet tissue. WT: tissues from wt mice; MPS II: tissues from non-treated MPS II mice; 1 wk pi/1 m pi: tissues from vector-treated MPS II mice. ˆ: p≤0.05 vs. WT; +: p>0.05 vs. WT; *: p≤0.05 vs. MPS II; #: p>0.05 vs. MPS II.
Figure 4B:
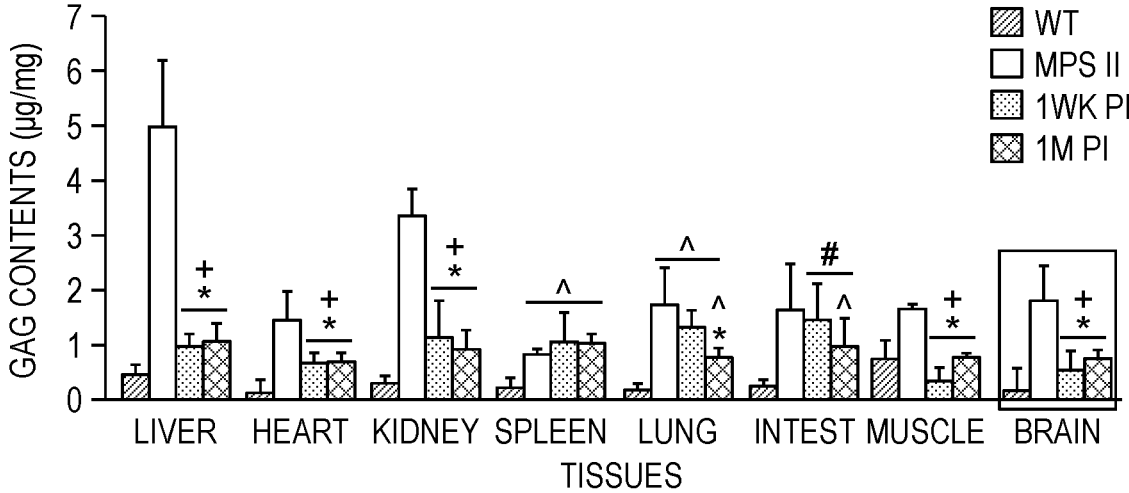

Rapid expression of functional IDS and clearance of lysosomal GAG storage in MPS II mice following an IV scAAV9-mCMV-hIDS$^{op}$ vector delivery: To assess the therapeutic potential of the novel scAAV9-mCMV-hIDS$^{op}$ vector product, 1 m-old MPS II mice were treated with the vector via an IV injection at $2 \times 10^{13}$ vg/kg. At 1 wk and 1 m post vector injection (pi), brain and multiple tissues were assayed for IDS activity (n=4/group), to determine the expression levels and the functionality of the recombinant IDS (rIDS). Tissues were also assayed for GAG contents to determine the impact of rIDS on the lysosomal accumulation of GAGs. The vector treatment resulted in rapid restoration of IDS activity to supranormal levels in the liver and heart, close to normal levels in kidney, spleen and lung, skeletal muscle, and intestine, and to 9% of WT levels in the brain at 1 m pi (FIG. 4A). Importantly, the vector treatment led to significant reduction in GAG contents to WT levels in the brain, liver, heart, kidney and skeletal muscle (FIG. 4B). These results demonstrate the rapid restoration of functional IDS protein in the CNS and broad peripheral tissues, leading to the clearance of lysosomal GAG storage in the central nervous system (CNS) and peripheral organs. These data strongly support the functional therapeutic potential of this novel scAAV9)-mCMV-hIDS$^{op}$ gene therapy product for the treatment of MPS II in humans.

Differential biodistribution of rAAV9-mCMV-hIDS vector genome: To determine the biodistribution of the systemically delivered scAAV9-mCMV-hIDS, total DNA isolated from tissues was assayed by qPCR to quantify scAAV9-hIDS vector genome copy numbers in tissues at different time points post vector injection (n≥4/group). The results showed differential biodistribution of the vector DNA among different tissues, with the highest concentration detected in the liver (Table 2).

TABLE 2

Bio-distribution of scAAV9-mCMV-
hIDS$^{op}$ in mice following a systemic delivery

| | Vg/dgDNA* (Means ± SD) | |
|---|---|---|
| Tissues | 1 wk pi | 1 m pi |
| Liver | 47.9183 ± 23.1496 | 85.2901 ± 42.1031 |
| Brain | 2.0879 ± 3.9317 | 0.4967 ± 0.4535 |
| Intestine | 0.2735 ± 0.1030 | 0.1190 ± 0.0347 |
| Heart | 1.0703 ± 0.7132 | 0.7090 ± 0.2501 |
| Kidney | 2.0917 ± 2.7352 | 0.3718 ± 0.0682 |
| Lung | 0.6951 ± 0.5132 | 0.1482 ± 0.0185 |
| Muscle | 5.3274 ± 3.1872 | 3.5790 ± 3.9698 |
| Spleen | 7.7224 ± 1.0048 | 0.3929 ± 0.2135 |

*Vg/dgDNA: vector genome per diploid genomic DNA.

To assess the therapeutic potential of scAAV9-mCMV-hIDS$^{op}$ gene delivery, the inventors have been performing dose-response experiments of the vector product in 1-2 m old MPS II mice, by an IV infusion, or the combination of an IV and an IT (intrathecal) delivery. For systemic delivery, MPS II mice were treated with an IV injection of scAAV9-mCMV-hIDS$^{op}$ vector at a dose of $5 \times 10^{11}$ vg/kg, $4 \times 10^{12}$ vg/kg, $1 \times 10^{13}$ vg/kg, or $2 \times 10^{13}$ vg/kg. For IV+IT deliver, MPS II mice were/will be treated with scAAV9-mCMV-hIDS$^{op}$ vector at different doses, via tail vein injection, followed by an infusion into the cistern magna.

Figures 5A, 5B:
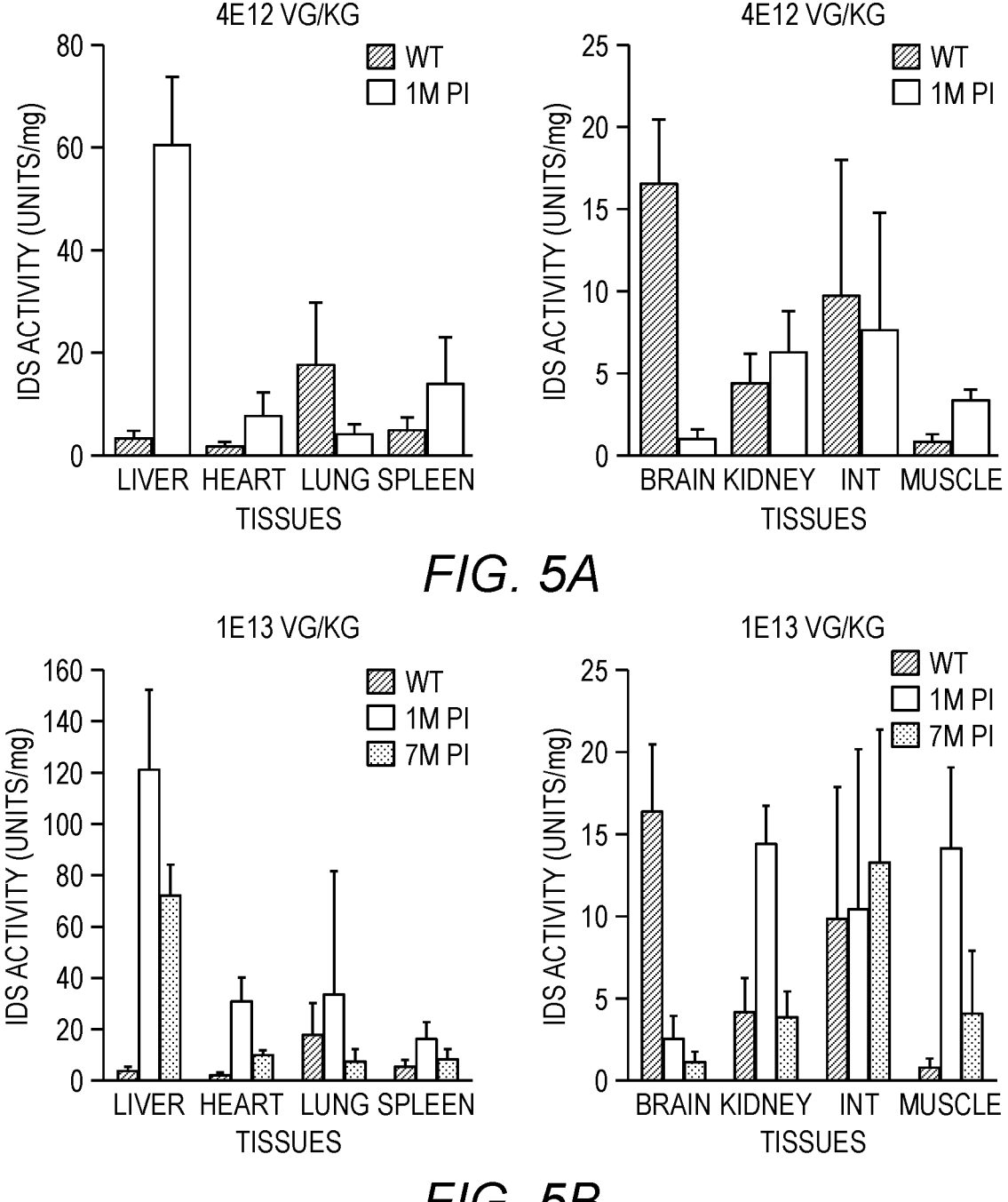
FIGS. 5A-5D show dose-dependent restoration of IDS activity in the CNS and peripheral tissues in MPS II mice following scAAV9-hIDS$^{op}$ gene delivery. MPS II mice were treated with different doses of scAAV9-mCMV-hIDS$^{op}$ at age 1-2 m via an IV injection (A-C) or an IV+IT infusions (D). At 1 m pi or 7 m pi, tissues (n=4/group) were assayed for IDS activity. IDS activity is expressed as units/mg protein, 1 unit=1 nmol 4 MU released/hr. WT: tissues from wt mice; 1 m pi/7 m pi: tissues from vector-treated MPS II mice.
Figures 5C, 5D:
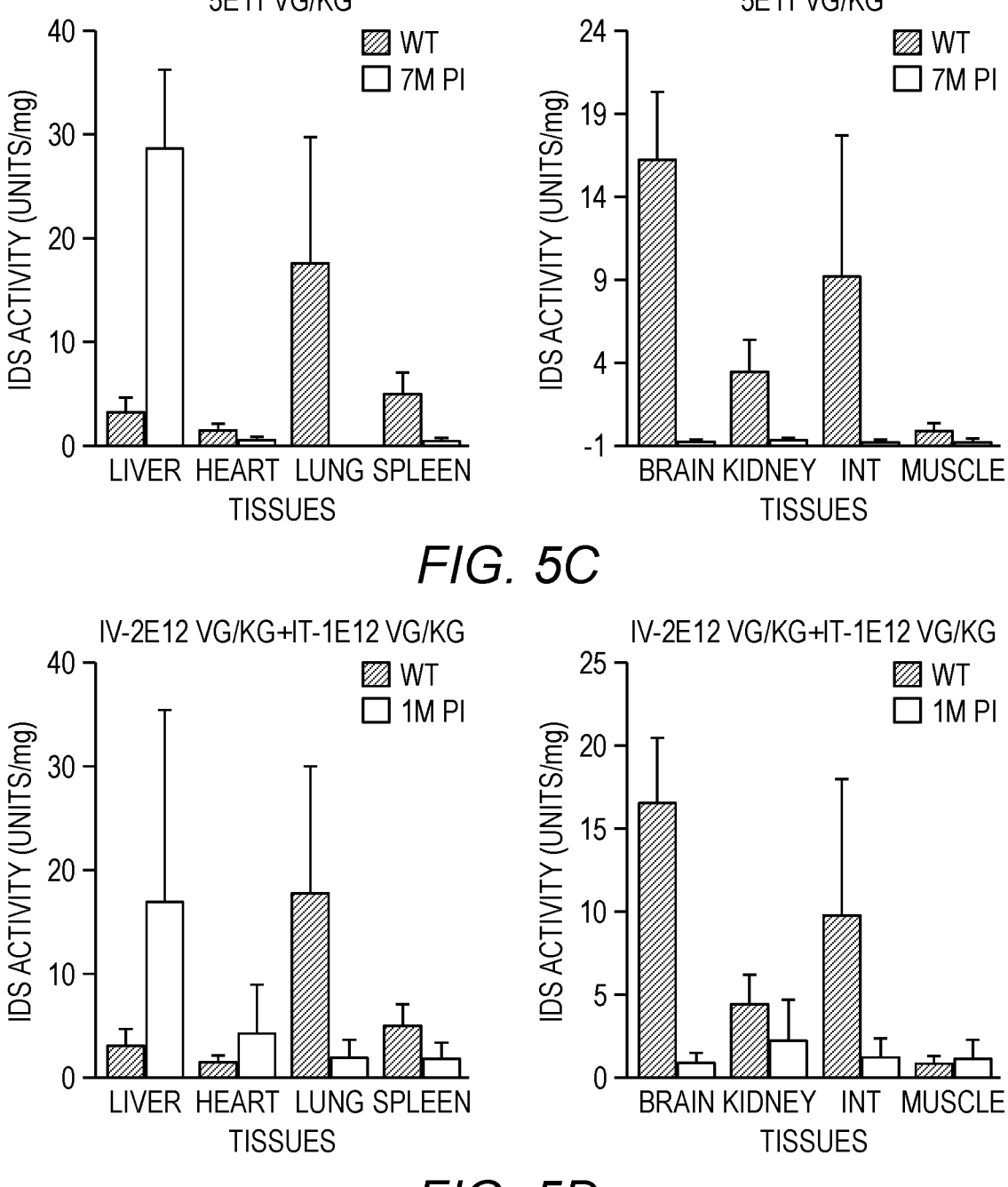

Necropsies were/will be performed for tissue analyses at 1 m post-injection (pi), 7 m pi, and/or humane endpoint (n≥4/group). Subsets of animals in each cohort were observed for longevity. Randomly assigned non-treated MPS II mice and their male wt littermates are used as controls. Table 3 summarizes the overall experimental design. The majority of the experiments are still ongoing and some are to be performed. To date, tissues analyzed were from mice treated with an IV vector injection at $5 \times 10^{11}$ vg/kg, $4 \times 10^{12}$ vg/kg and $1 \times 10^{13}$ vg/kg, and IV+IT injection at $2 \times 10^{12}$ vg/kg–$1 \times 10^{12}$ vg/kg.

for IDS activity (n=4/group) to determine the expression levels and the functionality of the recombinant IDS (rIDS). The results showed rapid and persistent expression of functional rIDS was dose-dependent following an IV vector treatment. IV vector injection at $4 \times 10^{12}$ vg/kg, resulted in rapid restoration of IDS activity to supranormal levels in the liver, heart, spleen and skeletal muscle, WT levels in kidney and intestine, and sub-normal levels in lung and to 6.4% of WT levels in the brain at 1 m pi (FIG. 5A). In mice given IV vector treatment at $1 \times 10^{13}$ vg/kg, much higher IDS activity was detected at supranormal levels in the liver, heart, spleen, kidney and skeletal muscle, WT levels in lung and intestine, and 16.4% of WT levels in the brain at 1 m pi (FIG. 5B), while reductions in tissue IDS activity were observed in all tested tissues with brain IDS activity to 8.1% of WT levels at 7 m pi. In contrast, an IV vector treatment at $5 \times 10^{11}$ vg/kg only resulted in the restoration of IDS activity to supranormal levels in the liver, but very low levels in other tested tissues, with <1% of WT levels in the brain when tested at 7 m pi (FIG. 5C). These data demonstrate that the restoration of tissue IDS activity is rapid, persistent, and dose-dependent in MPS II mice, following a systemic scAAV9-mCMV-hIDS$^{op}$ delivery. Further, IV vector treatment at $4 \times 10^{12}$ vg/kg and $1 \times 10^{13}$ vg/kg led to efficient restoration of IDS activity in the CNS and periphery, given the by-stander effects of IDS and previous observation that ≥3% WT IDS activity in the brain is functionally beneficial for treating MPS II neuropathy.

Further, combining an IV ($2 \times 10^{12}$ vg/kg) and IT ($1 \times 10^{12}$ vg/kg) injections, scAAV9-mCMV-hIDS$^{op}$ treatment resulted in the restoration of IDS activity to supranormal levels in the liver and heart, WT levels in muscle, and sub-normal but significant levels in spleen, kidney, lung, intestine, and brain. Notably the treatment led to brain IDS activity to 6% of WT levels, the same as that achieved by an IV injection at $4 \times 10^{12}$ vg/kg at 1 m pi (FIG. 5D). These data support the notion that combining IV with IT vector delivery may have significantly added CNS potential.

TABLE 3

Study design: systemic scAAV9-mCMV-hIDS$^{op}$ gene delivery in MPS II mice

| | | Vector | | Number of animals (n) | | | | |
|---|---|---|---|---|---|---|---|---|
| | Injection | Dose | | Behavior | | Necropsy | | |
| Mice | Route | (vg/kg) | Total | testing | 1 m pi | 7 m pi | End | Longevity |
| MPS II | IV* | $5 \times 10^{11}$ | 11 | 11** | — | 4* | ^ | 7*** |
| MPS II | IV* | $2 \times 10^{12}$ | 12 | 8^ | 4^ | — | ^ | 8*** |
| MPS II | IV* | $4 \times 10^{12}$ | 12 | 8** | 4* | — | ^ | 8*** |
| MPS II | IV* | $1 \times 10^{13}$ | 12 | 12** | 4* | 4* | ^ | 4*** |
| MPS II | IV* | $2 \times 10^{13}$ | 13 | 9^ | 4^ | 4^ | ^ | 5*** |
| MPS II | IV + IT* | $2 \times 10^{12} + 1 \times 10^{12}$ | 17 | 10^ | 4* | 4^ | ^ | 9*** |
| MPS II | IV + IT^ | $2 \times 10^{12} + 2 \times 10^{12}$ | ≥12 | ≥8^ | 4^ | 4^ | ^ | ≥4^ |
| MPS II | IV + IT^ | $5 \times 10^{12} + 2 \times 10^{12}$ | ≥12 | ≥8^ | 4^ | 4^ | ^ | ≥4^ |
| WT$^#$ | — | — | >86 | >83 | ≥4 | ≥4 | — | >74 |
| MPS II$^#$ | — | — | >24 | >20 | ≥4 | ≥4 | ≥4 | >18 |

Figure 6A:
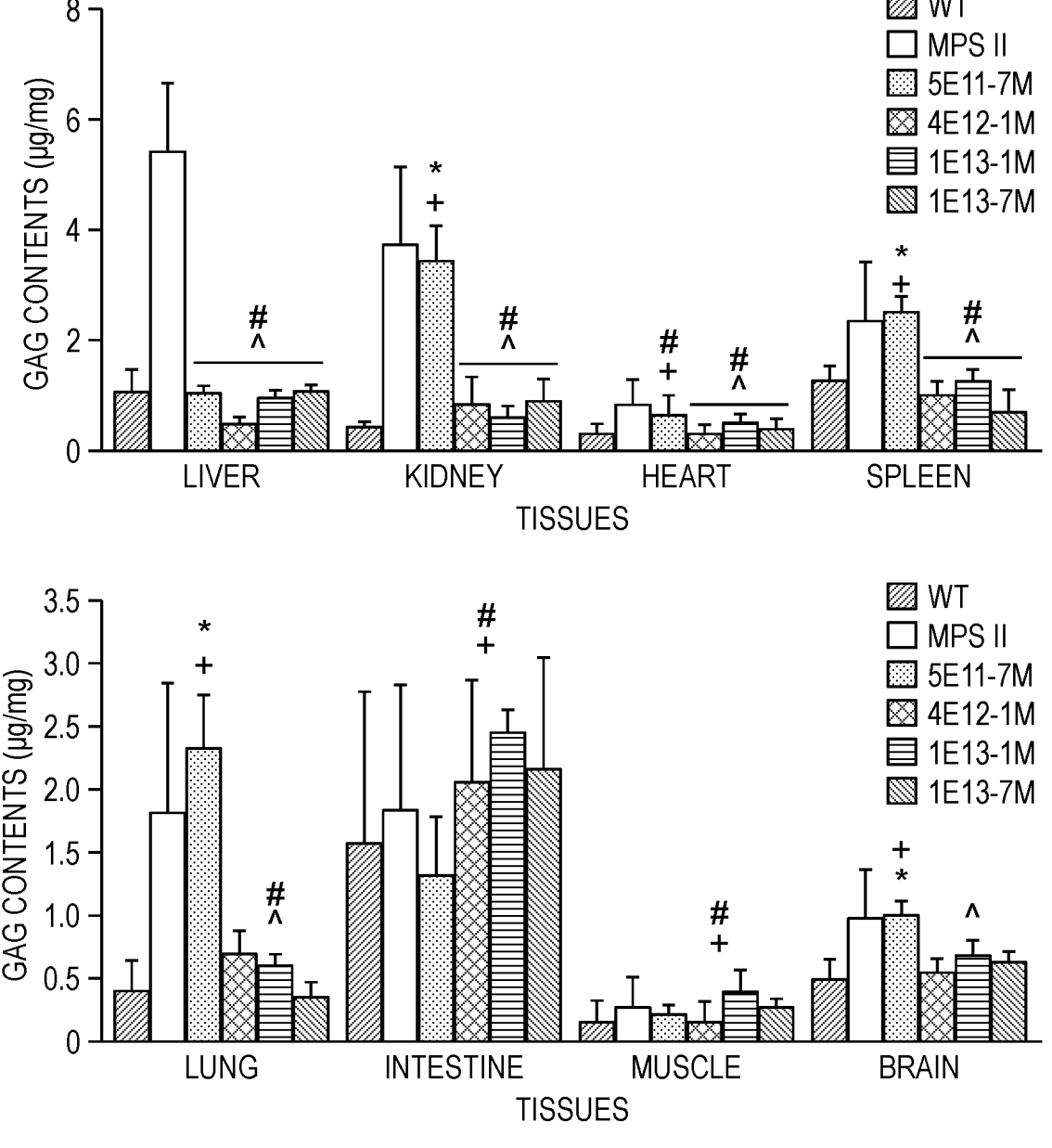
FIGS. 6A-6B show rapid and long-term clearance of lysosomal GAG storage in the CNS and peripheral tissues in MPS II mice following systemic scAAV9-hIDS$^{op}$ gene delivery. MPS II mice were treated with different doses of scAAV9-mCMV-hIDS$^{op}$ at age 1-2 m via an IV injection (A) or an IV+IT infusions (B). At 1 m pi or 7 m pi, tissues (n=4/group) were assayed for GAG contents. GAG content is expressed as µg/mg wet tissue. WT: tissues from wt mice; MPS II: tissues from non-treated MPS II mice; Others: tissues from vector-treated MPS II mice. *: p≤0.05 vs. WT; #: p>0.05 vs. WT; ˆ: p≤0.05 vs. MPS II; +: p>0.05 vs. MPS II.
Figure 6B:
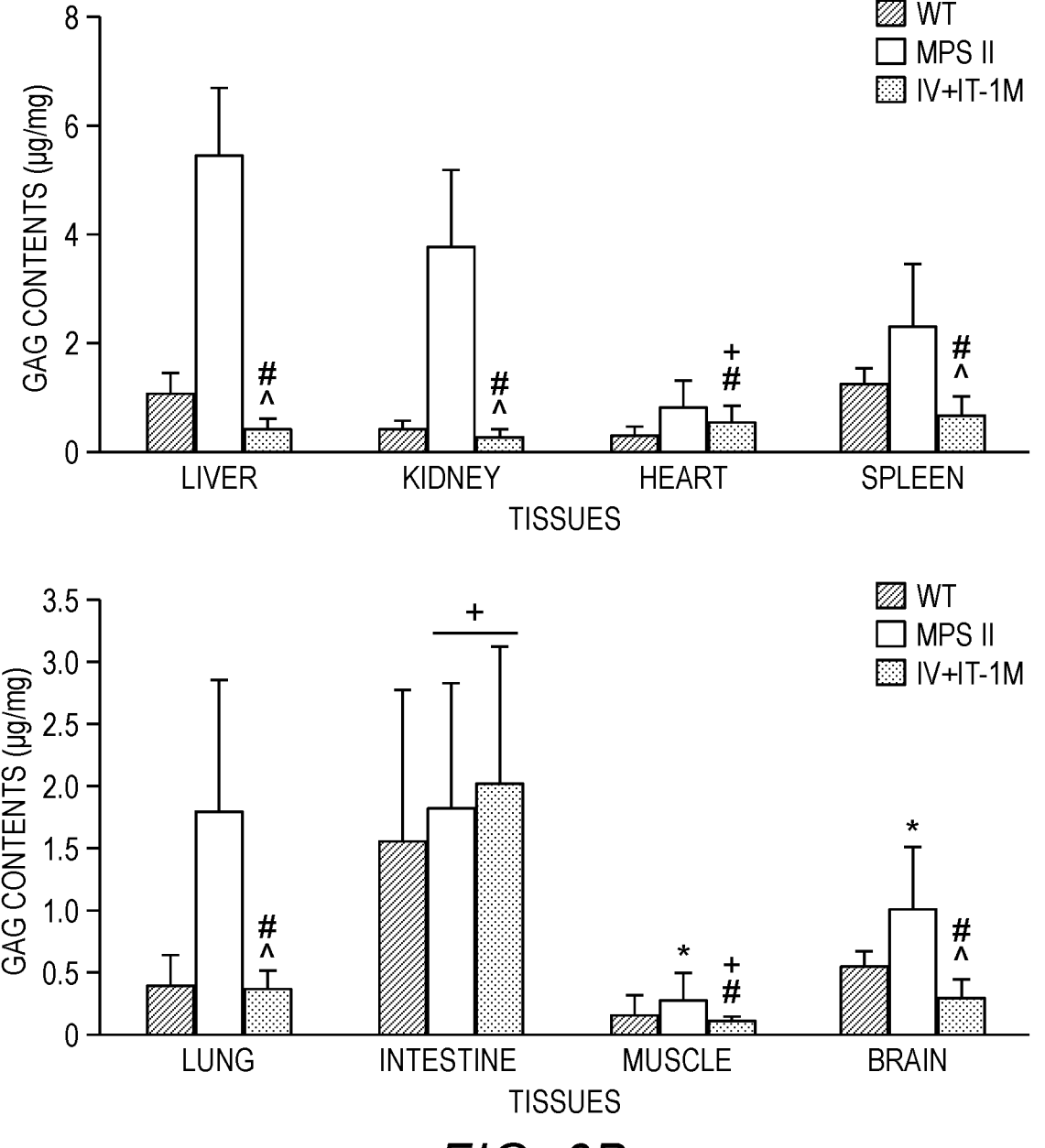

*Performed with data;
**performed-data analyses ongoing;
***ongoing;
^to be performed;
Controls: historically accumulated Rapid and persistent expression of functional IDS is dose-dependent: To assess the therapeutic potential of the scAAV9-mCMV-hIDS$^{op}$ vector product, 1-2 m old MPS II mice were treated with the vector at different doses via an IV injection or an IV+IT injection (Table 3). At 1 and 7 m post vector injection (pi), brain and multiple tissues were assayed Clearance of lysosomal GAG storage in MPS II mice following an IV scAAV9-mCMV-hIDS$^{op}$ vector delivery: To further assess the function of the rIDS, at 1 m and/or 7 m pi, brain and multiple tissues were assayed for GAG contents to determine the impact of rIDS on the lysosomal accumulation of GAGs. The results show that, as early as 1 m pi, the GAG contents were reduced to WT levels in the majority of tested tissues, including brain, liver, heart, spleen, kidney, and lung in MPS II mice treated with an IV injection of vector at $4\times10^{12}$ vg/kg or $1\times10^{13}$ vg/kg (FIG. 6A), or by combined IV ($2\times10^{12}$ vg/kg) and IT ($1\times10^{12}$ vg/kg) injections (FIG. 6B). Importantly, the tissue GAG reduction persisted to 7 m pi (FIG. 6A). No differences were observed in intestinal GAG contents among WT, non-treated MPS II and vector-treated MPS II mice, likely due to the sugar components ingested from food. Notably, correlating to tissue rIDS expression Differential biodistribution of rAAV9-mCMV-hIDS$^{op}$ vector genome: To determine the biodistribution of the systemically delivered scAAV9-mCMV-hIDS$^{op}$, total DNA isolated from tissues was assayed by qPCR to quantify scAAV9-hIDS vector genome copy numbers in tissues at different time points post vector injection (n≥4/group). The results showed differential biodistribution of the vector DNA among different tissues, with the highest concentration detected in the liver (Table 4). Further, the vector biodistribution appears to be dose-dependent, in general (Table 4).

TABLE 4

Bio-distribution of scAAV9-mCMV-hIDS$^{op}$ in mice following a systemic delivery

| Tissues | Vg/dgDNA* (Means ± SD) | | | |
| --- | --- | --- | --- | --- |
| | IV 5 × $10^{11}$ vg/kg 7 m pi | IV 4 × $10^{12}$ vg/kg 1 m pi | IV 1 × $10^{13}$ vg/kg 1 m pi | IV + IT** 1 m pi |
| Liver | 0.857 ± 0.198 | 7.342 ± 3.715 | 59.661 ± 22.581 | 0.961 ± 0.865 |
| Brain | 0.022 ± 0.011 | 1.709 ± 2.992 | 1.242 ± 1.708 | 0.132 ± 0.152 |
| Intestine | 0.247 ± 0.476 | 0.219 ± 0.224 | 0.092 ± 0.025 | 0.002 ± 0.002 |
| Heart | 0.073 ± 0.071 | 0.540 ± 0.373 | 1.029 ± 0.386 | 0.854 ± 0.858 |
| Kidney | 0.042 ± 0.044 | 0.246 ± 0.265 | 0.369 ± 0.077 | 0.382 ± 0.557 |
| Lung | 0.003 ± 0.004 | 0.057 ± 0.022 | 0.125 ± 0.019 | 0.053 ± 0.059 |
| Muscle | 0.052 ± 0.022 | 0.874 ± 0.619 | 0.608 ± 0.226 | 0.339 ± 0.295 |
| Spleen | 0.005 ± 0.007 | 0.090 ± 0.054 | 0.603 ± 0.479 | 0.411 ± 0.820 |

*Vg/dgDNA: vector genome per diploid genomic DNA.
**IV + IT: combine an IV (2 × $10^{12}$ vg/kg) and an IT (2 × $10^{12}$ vg/kg) infusion.

levels, an IV vector treatment at $4\times10^{11}$ vg/kg resulted in the decrease of GAG contents only in the liver, but not in the brain and other tested tissues (FIG. 6A). These results demonstrate, at effective doses, the rapid restoration of functional rIDS protein in the CNS and broad peripheral tissues, leading to the clearance of lysosomal GAG storage in both the CNS and peripheral organs. These data strongly support the functional therapeutic potential of this novel scAAV9-mCMV-hIDS$^{op}$ gene therapy product for the treatment of MPS II in humans.

Functional benefits: extension in survival: To assess the functional benefits of systemic scAAV9-mCMV-hIDS$^{op}$ gene therapy, the animals were/will be tested at age 8 m for cognitive behavior in the Morris water maze, and a subset of each cohort is observed for longevity. No final behavioral data are available and all pre-clinical experiments in MPS II mice are still ongoing.

Figure 7:
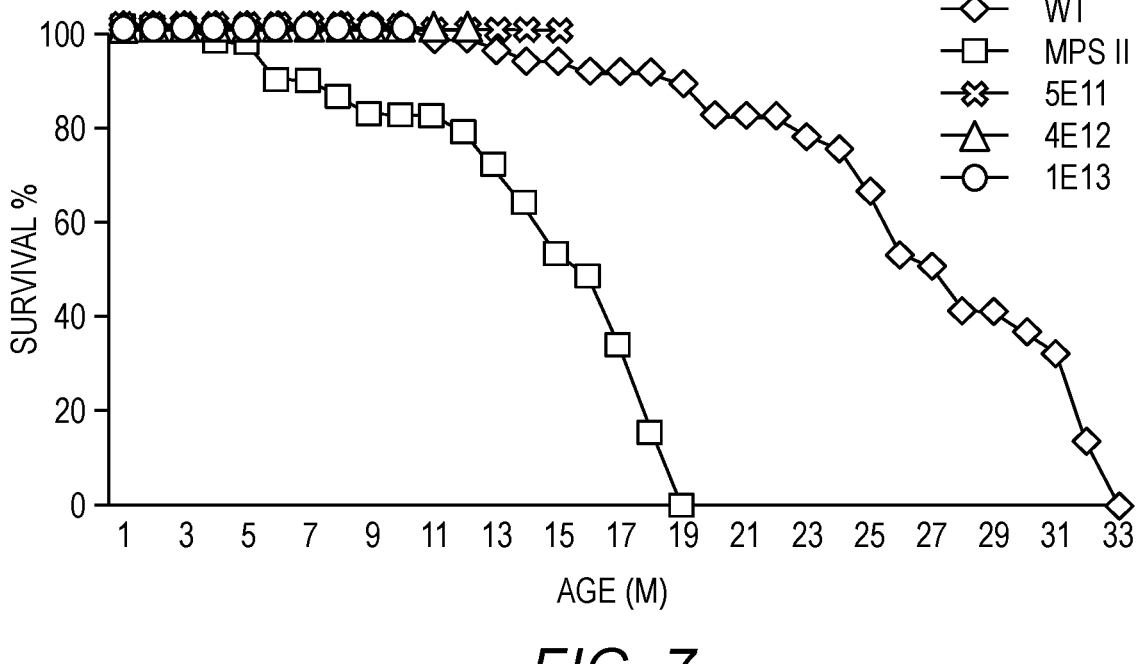
FIG. 7 shows survival of MPS II mice following systemic delivery of scAAV9-mCMV-hIDS$^{op}$. MPS II mice were treated with an IV injection of $5 \times 10^{11}$ vg/kg, $4 \times 10^{12}$ vg/kg, or $1 \times 10^{13}$ vg/kg scAAV9-mCMV-hIDS$^{op}$ vector at age 1-2 m. Subsets of animals were observed for longevity. WT and non-treated MPS II mice were used as controls.

To date, no deaths were observed in MPS II mice treated with an IV vector injection at $4\times10^{12}$ vg/kg or $1\times10^{13}$ vg/kg, at ages when there are 20-40% deaths in non-treated MPS II control mice (FIG. 7). Similar results were seen in mice treated IV with vector at $5\times10^{11}$ vg/kg. It is too early to make a final conclusion on the impact of the vector treatments on survival although the trend is towards increased survival. However, the results of the restoration of IDS activity (FIGS. 5A-5D) and clearance of GAG storage (FIGS. 6A-6B) in the CNS and peripheral organs support the long-term functional benefits of an IV vector injection at $4\times10^{12}$ vg/kg or $1\times10^{13}$ vg/kg, and combined IV ($2\times10^{12}$ vg/kg) and IT ($1\times10^{12}$ vg/kg) injections, based on our previous studies in systemic AAV9 gene delivery for MPS II, MPS IIIA and MPS IIIB.

The first generation rAAV gene replacement therapy vector expressing wt hIDS (scAAV9-mCMV-hIDS) has been demonstrated to be functionally beneficial for life (Fu et al., Mol. Ther. Meth. Clin. Dev. 10:327 (2018)). It can halt and reverse the disease progression with lifelong benefits via a single systemic delivery. To further improve the therapeutic efficacy of rAAV9-hIDS gene delivery, a second generation AAV gene therapy drug product was developed, scAAV9-mCMV-hIDSop, to deliver a codon-optimized hIDS gene (hIDSop). This new gene therapy product is an effective self-complementary AAV vector. The codon-optimization has resulted in significantly enhanced expression and secretion of the rIDS protein in human cells. The new scAAV9-mCMV-hIDSop vector led to the rapid restoration of IDS activity and clearance of lysosomal GAG storage in the CNS and peripheral tissues in MPS II mice via a single systemic delivery. It is believed that the new second generation scAAV9-hIDSop gene therapy vectors will significantly improve the therapeutic efficacy of scAAV9-hIDS gene replacement therapy for the treatment of MPS II, given that the efficacy and safety profiles of rAAV9 gene replacement therapy is highly reproducible across species and disease. The new vector product addresses the urgent unmet medical needs for MPS II and offers great potential of significantly improving the quality of life of not only MPS II patients but also their families.

The foregoing is illustrative of the present invention, and is not to be construed as limiting thereof. The invention is defined by the following claims, with equivalents of the claims to be included therein.

Sequences

SEQ ID NO: 1:
codon-optimized human IDS
```
ATGCCACCGC CAAGAACGGG CAGGGGTCTT CTGTGGCTGG GTCTTGTTTT GAGTAGTGTC

TGTGTGGCCC TCGGTAGTGA GACCCAGGCT AACAGCACAA CAGACGCGCT CAATGTCTTG

CTCATTATTG TTGATGATCT TAGACCCAGC TTGGGGTGCT ACGGGGATAA ACTCGTAAGG

TCACCGAACA TTGATCAGCT GGCATCACAT TCCCTTCTCT TCCAAAATGC GTTTGCGCAG

CAAGCCGTAT GCGCACCAAG TAGGGTTTCT TTCCTTACGG GCCGACGGCC AGATACGACA

CGGCTCTACG ACTTTAATTC CTACTGGCGC GTACACGCAG GGAACTTTAG CACGATCCCC

CAGTATTTTA AGGAGAACGG TTACGTCACA ATGAGCGTTG GGAAAGTTTT TCACCCTGGG

ATTAGTAGCA ACCATACAGA CGACAGTCCC TACTCATGGT CATTCCCACC TTACCATCCT

AGCAGCGAAA AATACGAAAA CACCAAAACT TGCCGCGGAC CTGATGGAGA ACTTCATGCC

AACCTCCTCT GCCCCGTTGA CGTACTCGAC GTCCCTGAGG GCACTCTCCC CGACAAACAA

AGCACAGAAC AGGCGATTCA GCTCCTGGAA AAAATGAAAA CGTCCGCATC ACCATTTTTT

TTGGCTGTTG GTTACCATAA GCCTCATATC CCTTTTAGAT ATCCCAAAGA ATTTCAGAAA

CTCTACCCAC TTGAGAATAT AACTTTGGCG CCAGATCCAG AGGTGCCAGA TGGTCTGCCC

CCTGTTGCTT ACAACCCCTG GATGGATATT CGACAAAGGG AAGACGTCCA AGCGCTCAAC

ATCTCTGTTC CCTATGGTCC GATACCAGTT GACTTCCAAA GAAAGATACG CCAATCATAC

TTTGCGAGTG TCAGTTATCT CGATACCCAA GTAGGTAGGC TGCTGAGTGC CCTCGACGAC

CTCCAGCTGG CTAACAGTAC CATCATAGCT TTTACCAGCG ACCACGGCTG GGCTCTGGGG

GAGCACGGGG AGTGGGCCAA ATATAGCAAC TTTGACGTGG CTACTCACGT ACCACTTATA

TTTTACGTAC CGGGTCGCAC GGCCTCTCTT CCCGAAGCCG GGGAAAAGCT TTTCCCTTAC

CTCGACCCCT TCGATTCCGC GTCACAACTG ATGGAGCCAG AAGACAGAG CATGGACCTG

GTCGAACTGG TGAGCCTGTT CCCTACACTC GCAGGGCTGG CAGGGCTGCA GGTCCCTCCA

CGCTGCCCAG TCCCTAGCTT TCATGTTGAA CTCTGTAGAG AGGGTAAAAA CCTGCTCAAG

CATTTCAGGT TCCGCGATCT TGAGGAAGAT CCCTATCTCC CTGGAAACCC GCGAGAACTG

ATTGCATATA GTCAGTATCC ACGCCCAAGT GACATCCCCC AGTGGAACTC AGACAAACCA

AGCCTTAAGG ATATTAAAAT TATGGGCTAT TCAATTAGGA CAATAGACTA TCGGTACACC

GTGTGGGTCG GGTTTAATCC TGACGAGTTC TTGGCAAACT TCAGTGATAT CCATGCTGGC

GAACTTTATT TCGTGGATTC AGATCCCCTC CAAGACCACA ATATGTATAA CGATAGCCAA

GGAGGAGACC TGTTTCAGCT GCTCATGCCT TGA
```

SEQ ID NO: 2:
wild-type human IDS
```
ATGCCGCCAC CCCGGACCGG CCGAGGCCTT CTCTGGCTGG GTCTGGTTCT GAGCTCCGTC

TGCGTCGCCC TCGGATCCGA AACGCAGGCC AACTCGACCA CAGATGCTCT GAACGTTCTT

CTCATCATCG TGGATGACCT GCGCCCCTCC CTGGGCTGTT ATGGGGATAA GCTGGTGAGG

TCCCCAAATA TTGACCAACT GGCATCCCAC AGCCTCCTCT TCCAGAATGC CTTTGCGCAG

CAAGCAGTGT GCGCCCCGAG CCGCGTTTCT TTCCTCACTG GCAGGAGACC TGACACCACC

CGCCTGTACG ACTTCAACTC CTACTGGAGG GTGCACGCTG GAAACTTCTC CACCATCCCC

CAGTACTTCA AGGAGAATGG CTATGTGACC ATGTCGGTGG GAAAAGTCTT TCACCCTGGG

ATATCTTCTA ACCATACCGA TGATTCTCCG TATAGCTGGT CTTTTCCACC TTATCATCCT

TCCTCTGAGA AGTATGAAAA CACTAAGACA GTGCGAGGGC CAGATGGAGA ACTCCATGCC

AACCTGCTTT GCCCTGTGGA TGTGCTGGAT GTTCCCGAGG GCACCTTGCC TGACAAACAG
```

-continued

| Sequences |
| --- |

```
AGCACTGAGC AAGCCATACA GTTGTTGGAA AAGATGAAAA CGTCAGCCAG TCCTTTCTTC

CTGGCCGTTG GGTATCATAA GCCACACATC CCCTTCAGAT ACCCCAAGGA ATTTCAGAAG

TTGTATCCCT TGGAGAACAT CACCCTGGCC CCCGATCCCG AGGTCCCTGA TGGCCTACCC

CCTGTGGCCT ACAACCCCTG GATGGACATC AGGCAACGGG AAGACGTCCA AGCCTTAAAC

ATCAGTGTGC CGTATGGTCC AATTCCTGTG GACTTTCAGC GGAAAATCCG CCAGAGCTAC

TTTGCCTCTG TGTCATATTT GGATACACAG TCGGCCGCC TCTTGAGTGC TTTGGACGAT

CTTCAGCTGG CCAACAGCAC CATCATTGCA TTTACCTCGG ATCATGGGTG GGCTCTAGGT

GAACATGGAG AATGGGCCAA ATACAGCAAT TTTGATGTTG CTACCCATGT TCCCCTGATA

TTCTATGTTC CTGGAAGGAC GGCTTCACTT CCGGAGGCAG GCGAGAAGCT TTTCCCTTAC

CTCGACCCTT TTGATTCCGC CTCACAGTTG ATGGAGCCAG GCAGGCAATC CATGGACCTT

GTGGAACTTG TGTCTCTTTT TCCCACGCTG GCTGGACTTG CAGGACTGCA GGTTCCACCT

CGCTGCCCCG TTCCTTCATT TCACGTTGAG CTGTGCAGAG AAGGCAAGAA CCTTCTGAAG

CATTTTCGAT TCCGTGACTT GGAAGAGGAT CCGTACCTCC CTGGTAATCC CCGTGAACTG

ATTGCCTATA GCCAGTATCC CCGGCCTTCA GACATCCCTC AGTGGAATTC TGACAAGCCG

AGTTTAAAAG ATATAAAGAT CATGGGCTAT TCCATACGCA CCATAGACTA TAGGTATACT

GTGTGGGTTG GCTTCAATCC TGATGAATTT CTAGCTAACT TTTCTGACAT CCATGCAGGG

GAACTGTATT TTGTGGATTC TGACCCATTG CAGGATCACA ATATGTATAA TGATTCCCAA

GGTGGAGATC TTTTCCAGTT GTTGATGCCT TGA
```

SEQ ID NO: 3:
scAAV-mCMV-hIDS<sup>op</sup>
```
CTGCGCGCTC GCTCGCTCAC TGAGGCCGCC CGGGCAAAGC CCGGGCGTCG GCGACCTTT

GGTCGCCCGG CCTCAGTGAG CGAGCGAGCG CGCAGAGAGG GAGTGGGGTT TAAACCTAAA

AAACCTCCCA CACCTCCCCC TGAACCTGAA ACATAAAATG AATGCAATTG TTGTTGTTAA

CTTGTTTATT GCAGCTTATA ATGGTTACAA ATAAAGCAAT AGCATCACAA ATTTCACAAA

TAAAGCATTT TTTTCACTGC ATTCTAGTTG TGGTTTGTCC AAACTCATCA ATGTATCTTA

TCATGTCTGA GATCTTCAGG GCATAAGAAG TTGAAACAAA TCCCCGCCCT GGCTATCGTT

GTACATGTTA TGATCTTGCA AGGGATCGCT ATCTACGAAA TACAACTCTC CAGCGTGAAT

GTCGCTAAAG TTAGCCAAAA ACTCATCTGG GTTAAAACCT ACCCAGACAG TATAGCGGTA

ATCAATCGTC CGTATGGAAT ATCCCATGAT TTTAATATCT TTAAGTGATG GTTTATCGGA

GTTCCATTGT GGAATATCGG ATGGCCTTGG ATACTGTGAA TAAGCAATAA GCTCTCGCGG

ATTACCTGGC AGGTATGGGT CCTCCTCAAG GTCCCTAAAC CGAAAGTGTT TCAACAAATT

CTTTCCCTCT CGGCACAGTT CTACATGGAA AGACGGCACA GGACATCTAG GTGGGACCTG

CAATCCGGCG AGCCCCGCCA GAGTTGGGAA AAGGGATACC AGCTCAACAA GGTCCATAGA

TTGTCGTCCA GGCTCCATGA GCTGGCTTGC GGAATCAAAT GGGTCGAGGT ACGGAAACAG

TTTTTCACCG GCTTCTGGCA AAGAAGCCGT CCGCCCAGGC ACATAAAATA TCAGAGGGAC

GTGCGTGGCG ACGTCAAAAT TAGAATATTT TGCCCATTCA CCATGCTCTC CGAGTGCCCA

GCCGTGATCG GACGTAAAAG CTATGATAGT GCTATTAGCC AACTGGAGAT CGTCCAATGC

ACTCAAAAGC CTTCCGACCT GAGTGTCAAG GTAGCTTACA GACGCGAAGT AGCTTTGTCG

GATTTTTCTC TGGAAATCTA CTGGAATCGG GCCATAAGGA ACACTGATGT TGAGAGCTTG
```

-continued

| Sequences |
| --- |

GACATCTTCC CTTTGCCTAA TGTCCATCCA AGGATTATAC GCCACCGGCG GCAGCCCATC

GGGGACCTCC GGGTCCGGAG CGAGCGTGAT ATTTTCAAGA GGATAGAGTT TCTGGAATTC

TTTCGGGTAT CTAAAGGGAA TATGCGGTTT GTGGTAGCCG ACGGCCAGGA AAAAAGGGGA

GGCGCTGGTC TTCATCTTCT CGAGCAACTG AATGGCCTGT TCGGTGCTTT GCTTGTCAGG

CAGTGTCCCT TCTGGAACGT CAAGTACGTC GACAGGGCAA AGCAAATTCG CATGCAACTC

TCCATCGGGC CCGCGACAAG TCTTTGTATT TTCGTATTTT TCGCTACTCG GATGGTAAGG

AGGGAAGCTC CATGAGTACG GGCTGTCGTC CGTGTGATTG GAACTAATTC CAGGATGAAA

TACCTTTCCC ACGCTCATAG TCACGTACCC GTTTTCTTTG AAGTACTGGG GAATCGTAGA

GAAATTCCCC GCATGAACCC GCCAATAGGA ATTAAAATCG TAAAGTCGCG TGGTGTCTGG

TCGCCGCCCA GTCAGAAATG AGACTCGTGA TGGCGCGCAA ACTGCTTGCT GAGCGAAAGC

ATTTTGAAAA AGGAGGGAAT GTGACGCGAG CTGATCGATG TTGGGGGATC TTACCAGCTT

ATCTCCGTAG CAGCCCAGGC TAGGGCGCAA GTCATCTACA ATTATCAGCA ATACATTGAG

CGCATCCGTG GTGCTATTCG CCTGGGTCTC GGACCCGAGG GCAACACAAA CGGATGACAG

AACCAATCCC AACCACAGCA AGCCCCGTCC AGTCCGTGGT GGAGGCATGA TGGGGCGACC

GGTCGAGCGG TTCACTAAAC GAGCTCTGCT TATATAGACC TCCCACCGTA CACGCCTACC

GCCCATTTGC GTCAATGGGG CGGAGTTGTT ACGACATTTT GGAAAGTCCC GTTGATTTTG

GTGCCAAAAC AAACTCCCAT TGACGTCAAT GGGGTGGAGA CTTGGAAATC CCCGTGAGTC

CGGGGGTCGT TGGGCGGTCA GCCAGGCGGG CCATTTACCG TAAGTTATGT AACGAAAGCT

TCCTAGGAAC CCCTAGTGAT GGAGTTGGCC ACTCCCTCTC TGCGCGCTCG CTCGCTCACT

GAGGCCGGGC GACCAAAGGT CGCCCGACGC CCGGGCTTTG CCCGGGCGGC CTCAGTGAGC

GAGCGAGCGC GCAG

SEQ ID NO: 4:
ptrsk-mCMV-hIDS$^{op}$
CAGCAGCTGC GCGCTCGCTC GCTCACTGAG GCCGCCCGGG CAAAGCCCGG GCGTCGGGCG

ACCTTTGGTC GCCCGGCCTC AGTGAGCGAG CGAGCGCGCA GAGAGGGAGT GGGGTTTAAA

CCTAAAAAAC CTCCCACACC TCCCCCTGAA CCTGAAACAT AAAATGAATG CAATTGTTGT

TGTTAACTTG TTTATTGCAG CTTATAATGG TTACAAATAA AGCAATAGCA TCACAAATTT

CACAAATAAA GCATTTTTTT CACTGCATTC TAGTTGTGGT TTGTCCAAAC TCATCAATGT

ATCTTATCAT GTCTGAGATC TTCAGGGCAT AAGAAGTTGA AACAAATCCC CGCCCTGGCT

ATCGTTGTAC ATGTTATGAT CTTGCAAGGG ATCGCTATCT ACGAAATACA ACTCTCCAGC

GTGAATGTCG CTAAAGTTAG CCAAAAACTC ATCTGGGTTA AAACCTACCC AGACAGTATA

GCGGTAATCA ATCGTCCGTA TGGAATATCC CATGATTTTA ATATCTTTAA GTGATGGTTT

ATCGGAGTTC CATTGTGGAA TATCGGATGG CCTTGGATAC TGTGAATAAG CAATAAGCTC

TCGCGGATTA CCTGGCAGGT ATGGGTCCTC CTCAAGGTCC CTAAACCGAA AGTGTTTCAA

CAAATTCTTT CCCTCTCGGC ACAGTTCTAC ATGGAAAGAC GGCACAGGAC ATCTAGGTGG

GACCTGCAAT CCGGCGAGCC CCGCCAGAGT TGGGAAAAGG GATACCAGCT CAACAAGGTC

CATAGATTGT CGTCCAGGCT CCATGAGCTG GCTTGCGGAA TCAAATGGGT CGAGGTACGG

AAACAGTTTT TCACCGGCTT CTGGCAAAGA AGCCGTCCGC CCAGGCACAT AAAATATCAG

AGGGACGTGC GTGGCGACGT CAAAATTAGA ATATTTTGCC CATTCACCAT GCTCTCCGAG

TGCCCAGCCG TGATCGGACG TAAAAGCTAT GATAGTGCTA TTAGCCAACT GGAGATCGTC

-continued

| Sequences |
|---|

```
CAATGCACTC AAAAGCCTTC CGACCTGAGT GTCAAGGTAG CTTACAGACG CGAAGTAGCT

TTGTCGGATT TTTCTCTGGA AATCTACTGG AATCGGGCCA TAAGGAACAC TGATGTTGAG

AGCTTGGACA TCTTCCCTTT GCCTAATGTC CATCCAAGGA TTATACGCCA CCGGCGGCAG

CCCATCGGGG ACCTCCGGGT CCGGAGCGAG CGTGATATTT TCAAGAGGAT AGAGTTTCTG

GAATTCTTTC GGGTATCTAA AGGGAATATG CGGTTTGTGG TAGCCGACGG CCAGGAAAAA

AGGGGAGGCG CTGGTCTTCA TCTTCTCGAG CAACTGAATG GCCTGTTCGG TGCTTTGCTT

GTCAGGCAGT GTCCCTTCTG GAACGTCAAG TACGTCGACA GGGCAAAGCA AATTCGCATG

CAACTCTCCA TCGGGCCCGC GACAAGTCTT TGTATTTTCG TATTTTTCGC TACTCGGATG

GTAAGGAGGG AAGCTCCATG AGTACGGGCT GTCGTCCGTG TGATTGGAAC TAATTCCAGG

ATGAAATACC TTTCCCACGC TCATAGTCAC GTACCCGTTT TCTTTGAAGT ACTGGGGAAT

CGTAGAGAAA TTCCCCGCAT GAACCCGCCA ATAGGAATTA AAATCGTAAA GTCGCGTGGT

GTCTGGTCGC CGCCCAGTCA GAAATGAGAC TCGTGATGGC GCGCAAACTG CTTGCTGAGC

GAAAGCATTT TGAAAAAGGA GGGAATGTGA CGCGAGCTGA TCGATGTTGG GGGATCTTAC

CAGCTTATCT CCGTAGCAGC CCAGGCTAGG GCGCAAGTCA TCTACAATTA TCAGCAATAC

ATTGAGCGCA TCCGTGGTGC TATTCGCCTG GGTCTCGGAC CCGAGGGCAA CACAAACGGA

TGACAGAACC AATCCCAACC ACAGCAAGCC CCGTCCAGTC CGTGGTGGAG GCATGATGGG

GCGACCGGTC GAGCGGTTCA CTAAACGAGC TCTGCTTATA TAGACCTCCC ACCGTACACG

CCTACCGCCC ATTTGCGTCA ATGGGGCGGA GTTGTTACGA CATTTTGGAA AGTCCCGTTG

ATTTTGGTGC CAAAACAAAC TCCCATTGAC GTCAATGGGG TGGAGACTTG GAAATCCCCG

TGAGTCCGGG GGTCGTTGGG CGGTCAGCCA GGCGGGCCAT TTACCGTAAG TTATGTAACG

AAAGCTTCCT AGGAACCCCT AGTGATGGAG TTGGCCACTC CCTCTCTGCG CGCTCGCTCG

CTCACTGAGG CCGGGCGACC AAAGGTCGCC CGACGCCCGG GCTTTGCCCG GCGGCCTCA

GTGAGCGAGC GAGCGCGCAG CTGGCGTAAT AGCGAAGAGG CCCGCACCGA TCGCCCTTCC

CAACAGTTGC GCAGCCTGAA TGGCGAATGG CGATTCCGTT GCAATGGCTG GCGGTAATAT

TGTTCTGGAT ATTACCAGCA AGGCCGATAG TTTGAGTTCT TCTACTCAGG CAAGTGATGT

TATTACTAAT CAAAGAAGTA TTGCGACAAC GGTTAATTTG CGTGATGGAC AGACTCTTTT

ACTCGGTGGC CTCACTGATT ATAAAAACAC TTCTCAGGAT TCTGGCGTAC CGTTCCTGTC

TAAAATCCCT TTAATCGGCC TCCTGTTTAG CTCCCGCTCT GATTCTAACG AGGAAAGCAC

GTTATACGTG CTCGTCAAAG CAACCATAGT ACGCGCCCTG TAGCGGCGCA TTAAGCGCGG

CGGGTGTGGT GGTTACGCGC AGCGTGACCG CTACACTTGC CAGCGCCCTA GCGCCCGCTC

CTTTCGCTTT CTTCCCTTCC TTTCTCGCCA CGTTCGCCGG CTTTCCCCGT CAAGCTCTAA

ATCGGGGGCT CCCTTTAGGG TTCCGATTTA GTGCTTTACG GCACCTCGAC CCCAAAAAAC

TTGATTAGGG TGATGGTTCA CGTAGTGGGC CATCGCCCTG ATAGACGGTT TTTCGCCCTT

TGACGTTGGA GTCCACGTTC TTTAATAGTG GACTCTTGTT CCAAACTGGA ACAACACTCA

ACCCTATCTC GGTCTATTCT TTTGATTTAT AAGGGATTTT GCCGATTTCG GCCTATTGGT

TAAAAAATGA GCTGATTTAA CAAAAATTTA ACGCGAATTT TAACAAAATA TTAACGCTTA

CAATTTAAAT ATTTGCTTAT ACAATCTTCC TGTTTTTGGG GCTTTTCTGA TTATCAACCG

GGGTACATAT GATTGACATG CTAGTTTTAC GATTACCGTT CATCGATTCT CTTGTTTGCT
```

-continued

| Sequences |
| --- |

```
CCAGACTCTC AGGCAATGAC CTGATAGCCT TTGTAGAGAC CTCTCAAAAA TAGCTACCCT

CTCCGGCATG AATTTATCAG CTAGAACGGT TGAATATCAT ATTGATGGTG ATTTGACTGT

CTCCGGCCTT TCTCACCCGT TTGAATCTTT ACCTACACAT TACTCAGGCA TTGCATTTAA

AATATATGAG GGTTCTAAAA ATTTTTATCC TTGCGTTGAA ATAAAGGCTT CTCCCGCAAA

AGTATTACAG GGTCATAATG TTTTTGGTAC AACCGATTTA GCTTTATGCT CTGAGGCTTT

ATTGCTTAAT TTTGCTAATT CTTTGCCTTG CCTGTATGAT TTATTGGATG TTGGAATCGC

CTGATGCGGT ATTTTCTCCT TACGCATCTG TGCGGTATTT CACACCGCAT ATGGTGCACT

CTCAGTACAA TCTGCTCTGA TGCCGCATAG TTAAGCCAGC CCCGACACCC GCCAACACCC

GCTGACGCGC CCTGACGGGC TTGTCTGCTC CCGGCATCCG CTTACAGACA AGCTGTGACC

GTCTCCGGGA GCTGCATGTG TCAGAGGTTT TCACCGTCAT CACCGAAACG CGCGAGACGA

AAGGGCCTCG TGATACGCCT ATTTTTATAG GTTAATGTCA TGATAATAAT GGTTTCTTAG

ACGTCAGGTG GCACTTTTCG GGGAAATGTG CGCGGAACCC CTATTTGTTT ATTTTTCTAA

ATACATTCAA ATATGTATCC GCTCATGAGA CAATAACCCT GATAAATGCT TCAATAATAT

TGAAAAAGGA AGAGTATGAG TATTCAACAT TTCCGTGTCG CCCTTATTCC CTTTTTTGCG

GCATTTTGCC TTCCTGTTTT TGCTCACCCA GAAACGCTGG TGAAAGTAAA AGATGCTGAA

GATCAGTTGG GTGCACGAGT GGGTTACATC GAACTGGATC TCAACAGCGG TAAGATCCTT

GAGAGTTTTC GCCCCGAAGA ACGTTTTCCA ATGATGAGCA CTTTTAAAGT TCTGCTATGT

GGCGCGGTAT TATCCCGTAT TGACGCCGGG CAAGAGCAAC TCGGTCGCCG CATACACTAT

TCTCAGAATG ACTTGGTTGA GTACTCACCA GTCACAGAAA AGCATCTTAC GGATGGCATG

ACAGTAAGAG AATTATGCAG TGCTGCCATA ACCATGAGTG ATAACACTGC GGCCAACTTA

CTTCTGACAA CGATCGGAGG ACCGAAGGAG CTAACCGCTT TTTTGCACAA CATGGGGGAT

CATGTAACTC GCCTTGATCG TTGGGAACCG GAGCTGAATG AAGCCATACC AAACGACGAG

CGTGACACCA CGATGCCTGT AGCAATGGCA ACAACGTTGC GCAAACTATT AACTGGCGAA

CTACTTACTC TAGCTTCCCG GCAACAATTA ATAGACTGGA TGGAGGCGGA TAAAGTTGCA

GGACCACTTC TGCGCTCGGC CCTTCCGGCT GGCTGGTTTA TTGCTGATAA ATCTGGAGCC

GGTGAGCGTG GGTCTCGCGG TATCATTGCA GCACTGGGGC CAGATGGTAA GCCCTCCCGT

ATCGTAGTTA TCTACACGAC GGGGAGTCAG GCAACTATGG ATGAACGAAA TAGACAGATC

GCTGAGATAG GTGCCTCACT GATTAAGCAT TGGTAACTGT CAGACCAAGT TTACTCATAT

ATACTTTAGA TTGATTTAAA ACTTCATTTT TAATTTAAAA GGATCTAGGT GAAGATCCTT

TTTGATAATC TCATGACCAA AATCCCTTAA CGTGAGTTTT CGTTCCACTG AGCGTCAGAC

CCCGTAGAAA AGATCAAAGG ATCTTCTTGA GATCCTTTTT TTCTGCGCGT AATCTGCTGC

TTGCAAACAA AAAAACCACC GCTACCAGCG GTGGTTTGTT TGCCGGATCA AGAGCTACCA

ACTCTTTTTC CGAAGGTAAC TGGCTTCAGC AGAGCGCAGA TACCAAATAC TGTTCTTCTA

GTGTAGCCGT AGTTAGGCCA CCACTTCAAG AACTCTGTAG CACCGCCTAC ATACCTCGCT

CTGCTAATCC TGTTACCAGT GGCTGCTGCC AGTGGCGATA AGTCGTGTCT TACCGGGTTG

GACTCAAGAC GATAGTTACC GGATAAGGCG CAGCGGTCGG GCTGAACGGG GGGTTCGTGC

ACACAGCCCA GCTTGGAGCG AACGACCTAC ACCGAACTGA GATACCTACA GCGTGAGCTA

TGAGAAAGCG CCACGCTTCC CGAAGGGAGA AAGGCGGACA GGTATCCGGT AAGCGGCAGG

GTCGGAACAG GAGAGCGCAC GAGGGAGCTT CCAGGGGGAA ACGCCTGGTA TCTTTATAGT
```

-continued

| Sequences |
| --- |

CCTGTCGGGT TTCGCCACCT CTGACTTGAG CGTCGATTTT TGTGATGCTC GTCAGGGGGG

CGGAGCCTAT GGAAAAACGC CAGCAACGCG GCCTTTTTAC GGTTCCTGGC CTTTTGCTGG

CCTTTTGCTC ACATGTTCTT TCCTGCGTTA TCCCCTGATT CTGTGGATAA CCGTATTACC

GCCTTTGAGT GAGCTGATAC CGCTCGCCGC AGCCGAACGA CCGAGCGCAG CGAGTCAGTG

AGCGAGGAAG CGGAAGAGCG CCCAATACGC AAACCGCCTC TCCCCGCGCG TTGGCCGATT

CATTAATG

SEQ ID NO: 5:
hIDS<sup>op</sup>-2
ATGCCTCCCC CTAGGACGGG TCGGGGCCTC TTGTGGCTGG GCCTGGTACT GAGTTCAGTG

TGCGTAGCAC TGGGGAGCGA GACACAGGCC AACAGCACCA CGGACGCGCT TAACGTATTG

CTCATTATTG TTGATGATCT GCGCCCTAGT CTGGGTTGCT ACGGTGACAA ACTTGTTAGG

TCACCTAACA TAGACCAGCT GGCTAGTCAC AGCCTTCTTT TTCAAAATGC CTTTGCTCAA

CAAGCTGTAT GCGCCCCTAG TCGCGTGAGT TTCCTTACTG GTCGACGACC CGATACAACA

CGCCTTTATG ACTTTAACAG TTACTGGCGC GTCCATGCAG GCAACTTCTC AACGATACCG

CAGTACTTCA AGGAAAACGG CTACGTGACC ATGTCTGTTG GCAAGGTATT TCATCCTGGT

ATTTCAAGCA ACCATACAGA CGATTCTCCA TACTCTTGGT CATTTCCCCC ATATCACCCG

AGCTCTGAGA AATACGAAAA CACAAAAACA TGTAGAGGAC CGGACGGTGA GCTGCACGCA

AATTTGCTTT GCCCGGTCGA CGTACTCGAT GTCCCGGAGG GGACTCTTCC TGATAAGCAA

AGCACCGAAC AGGCAATCCA GCTGCTCGAA AAAATGAAGA CTAGCGCTTC ACCATTTTTT

CTCGCTGTGG GCTATCACAA ACCACACATC CCTTTTCGAT ATCCTAAAGA GTTTCAAAAA

CTCTACCCTC TCGAAAACAT TACTTTGGCC CCCGATCCCG AGGTCCCGGA CGGACTGCCA

CCCGTCGCGT ACAATCCCTG GATGGACATC CGGCAACGAG AAGACGTGCA AGCACTGAAT

ATTTCCGTGC CCTACGGGCC AATTCCTGTT GATTTTCAAA GGAAAATACG GCAGAGTTAT

TTTGCGTCCG TCTCATACCT TGACACGCAG GTAGGAAGGC TCCTTTCAGC TTTGGACGAT

TTGCAACTGG CAAATTCAAC AATTATAGCA TTCACTTCAG ACCACGGGTG GGCGCTCGGT

GAACACGGGG AGTGGGCTAA GTACTCCAAC TTTGACGTGG CGACACATGT ACCGCTTATA

TTTTACGTCC CTGGTAGAAC TGCGAGCCTC CCAGAGGCCG GAGAGAAGCT CTTCCCATAC

CTCGATCCTT TTGATTCTGC AAGTCAGTTG ATGGAGCCCG GACGACAAAG TATGGACCTT

GTTGAGCTCG TATCTCTGTT TCCAACGCTT GCTGGGCTGG CAGGGCTGCA AGTTCCTCCT

AGGTGTCCGG TTCCTTCCTT CCATGTTGAG CTCTGCAGAG AAGGGAAAAA CCTCCTCAAA

CATTTCCGAT TCAGGGACCT GGAGGAAGAT CCCTACTTGC CAGGGAATCC ACGAGAGCTG

ATAGCCTACT CACAGTATCC ACGGCCCAGT GATATCCCCC AATGGAACAG TGATAAGCCC

TCCCTGAAAG ATATCAAGAT AATGGGCTAT AGCATTAGAA CAATCGACTA CAGGTATACC

GTTTGGGTCG GTTTTAATCC CGATGAATTC CTGGCGAACT TCAGTGATAT CCACGCAGGA

GAGCTGTACT TCGTTGACTC CGATCCATTG CAGGATCACA ACATGTATAA TGATAGTCAG

GGCGGTGATC TTTTTCAGCT GCTTATGCCT TGA

SEQ ID NO: 6:
hIDS<sup>op</sup>-3
ATGCCTCCGC CTCGGACAGG ACGGGGACTG CTCTGGCTTG GGCTGGTGCT TAGCAGCGTC

TGTGTCGCTC TGGGCTCAGA AACCCAGGCG AATTCAACGA CAGACGCCCT GAACGTCTTG

-continued

| Sequences |
| --- |

CTTATTATAG TGGACGATCT GCGACCATCA TTGGGGTGTT ATGGGGATAA GTTGGTGCGA

TCTCCCAACA TTGACCAACT GGCTTCTCAC AGCCTCCTTT TCCAAAACGC TTTCGCGCAG

CAAGCGGTCT GCGCTCCTTC AAGAGTAAGC TTTCTCACAG GAAGACGCCC CGACACCACA

CGCTTGTACG ATTTTAACTC ATATTGGAGA GTTCATGCGG GGAACTTTTC AACCATCCCA

CAGTATTTTA AGGAGAATGG CTACGTCACG ATGAGTGTGG GAAAAGTATT CCATCCGGGC

ATTTCCAGCA ATCATACCGA TGATAGCCCT TATAGTTGGT CCTTCCCGCC CTACCACCCG

AGTTCCGAGA AGTATGAAAA TACTAAAACA TGCCGAGGCC CCGACGGTGA ATTGCATGCC

AACTTGCTCT GCCCCGTCGA TGTACTTGAC GTACCTGAGG GTACACTCCC CGATAAGCAG

TCTACGGAAC AAGCCATACA ACTGCTGGAA AAAATGAAGA CATCAGCTAG TCCGTTCTTC

TTGGCAGTTG GTTACCATAA GCCCCATATA CCATTTCGGT ATCCAAAGGA ATTTCAAAAG

TTGTATCCAC TGGAGAATAT AACCCTCGCC CCTGACCCGG AGGTCCCAGA CGGTCTCCCC

CCAGTTGCTT ACAACCCCTG GATGGATATT AGGCAGCGAG AAGACGTACA GGCTTTGAAT

ATCTCCGTAC CATACGGACC GATTCCCGTA GATTTCCAGC GAAAAATCCG CCAGTCCTAC

TTTGCGTCCG TATCATACCT GGACACTCAA GTTGGCAGAT TGCTTTCCGC ATTGGATGAT

CTGCAGTTGG CGAATAGCAC CATCATTGCT TTCACTAGCG ATCACGGATG GGCCCTGGGA

GAGCATGGTG AGTGGGCGAA GTATAGCAAC TTCGACGTCG CAACGCACGT GCCTCTCATT

TTTTACGTTC CTGGGCGAAC GGCTTCTTTG CCTGAAGCAG GGGAGAAGCT CTTCCCATAT

CTGGACCCCT TCGATAGCGC TTCTCAATTG ATGGAACCAG GACGGCAGAG CATGGATCTC

GTAGAACTGG TCTCACTTTT CCCGACCCTC GCGGGTCTTG CAGGACTCCA GGTCCCTCCT

CGGTGCCCTG TACCTAGTTT TCACGTGGAG CTGTGTAGGG AGGGGAAGAA CTTGCTCAAA

CATTTTAGGT TCCGGGACCT TGAGGAAGAT CCGTATCTGC CAGGTAATCC CAGAGAGCTT

ATCGCTTATA GTCAGTACCC ACGGCCGAGC GACATTCCCC AGTGGAATAG TGATAAGCCC

AGCTTGAAGG ACATTAAGAT AATGGGATAC AGCATTCGGA CTATAGACTA TCGGTACACT

GTCTGGGTCG GTTTTAACCC AGATGAATTT TTGGCTAATT TTTCAGACAT CCATGCTGGG

GAGCTTTATT TTGTAGATAG TGATCCTTTG CAAGATCATA ATATGTATAA CGACAGCCAA

GGTGGAGACT TGTTCCAATT GCTTATGCCA TGA

SEQ ID NO: 7:
hIDS^op-4
ATGCCACCGC CAAGAACGGG CAGGGGTCTT CTGTGGCTGG GTCTTGTTTT GAGTAGTGTC

TGTGTGGCCC TCGGTAGTGA GACCCAGGCT AACAGCACAA CAGACGCGCT CAATGTCTTG

CTCATTATTG TTGATGATCT TAGACCCAGC TTGGGGTGCT ACGGGGATAA ACTCGTAAGG

TCACCGAACA TTGATCAGCT GGCATCACAT TCCCTTCTCT TCCAAAATGC GTTTGCGCAG

CAAGCCGTAT GCGCACCAAG TAGGGTTTCT TTCCTTACGG GCCGACGGCC AGATACGACA

CGGCTCTACG ACTTTAATTC CTACTGGCGC GTACACGCAG GGAACTTTAG CACGATCCCC

CAGTATTTTA AGGAGAACGG TTACGTCACA ATGAGCGTTG GGAAAGTTTT TCACCCTGGG

ATTAGTAGCA ACCATACAGA CGACAGTCCC TACTCATGGT CATTCCCACC TTACCATCCT

AGCAGCGAAA AATACGAAAA CACCAAAACT TGCCGCGGAC CTGATGGAGA ACTTCATGCC

AACCTCCTCT GCCCCGTTGA CGTACTCGAC GTCCCTGAGG GCACTCTCCC CGACAAACAA

AGCACAGAAC AGGCGATTCA GCTCCTGGAA AAAATGAAAA CGTCCGCATC ACCATTTTTT

TTGGCTGTTG GTTACCATAA GCCTCATATC CCTTTTAGAT ATCCCAAAGA ATTTCAGAAA

-continued

Sequences

CTCTACCCAC TTGAGAATAT AACTTTGGCG CCAGATCCAG AGGTGCCAGA TGGTCTGCCC

CCTGTTGCTT ACAACCCCTG GATGGATATT CGACAAAGGG AAGACGTCCA AGCGCTCAAC

ATCTCTGTTC CCTATGGTCC GATACCAGTT GACTTCCAAA GAAAGATACG CCAATCATAC

TTTGCGAGTG TCAGTTATCT CGATACCCAA GTAGGTAGGC TGCTGAGTGC CCTCGACGAC

CTCCAGCTGG CTAACAGTAC CATCATAGCT TTTACCAGCG ACCACGGCTG GGCTCTGGGG

GAGCACGGGG AGTGGGCCAA ATATAGCAAC TTTGACGTGG CTACTCACGT ACCACTTATA

TTTTACGTAC CGGGTCGCAC GGCCTCTCTT CCCGAAGCCG GGGAAAAGCT TTTCCCTTAC

CTCGACCCCT TCGATTCCGC GTCACAACTG ATGGAGCCAG GAAGACAGAG CATGGACCTG

GTCGAACTGG TGAGCCTGTT CCCTACACTC GCAGGGCTGG CAGGGCTGCA GGTCCCTCCA

CGCTGCCCAG TCCCTAGCTT TCATGTTGAA CTCTGTAGAG AGGGTAAAAA CCTGCTCAAG

CATTTCAGGT TCCGCGATCT TGAGGAAGAT CCCTATCTCC CTGGAAACCC GCGAGAACTG

ATTGCATATA GTCAGTATCC ACGCCCAAGT GACATCCCCC AGTGGAACTC AGACAAACCA

AGCCTTAAGG ATATTAAAAT TATGGGCTAT TCAATTAGGA CAATAGACTA TCGGTACACC

GTGTGGGTCG GGTTTAATCC TGACGAGTTC TTGGCAAACT TCAGTGATAT CCATGCTGGC

GAACTTTATT TCGTGGATTC AGATCCCCTC CAAGACCACA ATATGTATAA CGATAGCCAA

GGAGGAGACC TGTTTCAGCT GCTCATGCCT TGA

That which is claimed is:

1. A recombinant nucleic acid comprising a sequence encoding human iduronate-2-sulfatase (IDS) that is codon-optimized for expression in human cells, wherein the recombinant nucleic acid comprises a nucleotide sequence at least 99% identical to SEQ ID NO:1.

2. The recombinant nucleic acid of claim 1, comprising the nucleotide sequence of SEQ ID NO:1.

3. A vector comprising the recombinant nucleic acid of claim 1.

4. The vector of claim 3, comprising the sequence of SEQ ID NO:4 or a sequence at least 90% identical thereto.

5. An adeno-associated virus (AAV) vector genome comprising the recombinant nucleic acid of claim 1.

6. The AAV vector genome of claim 5, wherein the AAV vector genome is a self-complementary AAV vector genome.

7. The AAV vector genome of claim 5, wherein the AAV vector genome comprises the sequence of SEQ ID NO:3 or a sequence at least 90% identical thereto.

8. The AAV vector genome of claim 5, wherein the recombinant nucleic acid is operably linked to a constitutive promoter.

9. The AAV vector genome of claim 8, wherein the constitutive promoter is a cytomegalovirus promoter.

10. A cell in vitro comprising the AAV vector genome of claim 5.

11. A method of producing a recombinant AAV particle comprising an AAV capsid, the method comprising:

providing a cell in vitro with AAV Cap and AAV Rep coding sequences, the AAV vector genome of claim 5, and helper functions for generating a productive AAV infection; and allowing assembly of the recombinant AAV particle comprising the AAV capsid and encapsidating the AAV vector genome.

12. An AAV particle comprising the AAV vector genome of claim 5.

13. The AAV particle of claim 12, wherein the AAV particle is an AAV9 particle.

14. A pharmaceutical formulation comprising the AAV particle of claim 12 and a pharmaceutically acceptable carrier.

15. A method of expressing IDS in a cell, comprising contacting the cell with an effective amount of the AAV particle of claim 12, thereby expressing IDS in the cell.

16. A method of increasing secretion of IDS from a cell, comprising contacting the cell with an effective amount of the AAV particle of claim 12, thereby increasing secretion of IDS from the cell relative to the secretion of IDS after contacting the cell with an AAV particle comprising a nucleic acid comprising the wild-type sequence for IDS.

17. A method of delivering IDS to a subject, comprising administering to the subject an effective amount of the AAV particle of claim 12, thereby delivering IDS to the subject.

18. A method of treating or delaying the onset of mucopolysaccharidosis II (MPS II) in a subject in need thereof, comprising administering to the subject a therapeutically effective amount of the AAV particle of claim 12, thereby treating or delaying the onset of MPS II in the subject.

19. The method of claim 18, wherein the subject is a human subject.

20. The method of claim 18, wherein the subject has been diagnosed with MPS II.

\* \* \* \* \*

SEQUENCE LISTING

<160> NUMBER OF SEQ ID NOS: 7

<210> SEQ ID NO 1
<211> LENGTH: 1653
<212> TYPE: DNA
<213> ORGANISM: Artificial sequence
<220> FEATURE:
<223> OTHER INFORMATION: Synthetic polynucleotide

<400> SEQUENCE: 1
atgccaccgc caagaacggg cagggggtctt ctgtggctgg gtcttgtttt gagtagtgtc      60
tgtgtggccc tcggtagtga gacccaggct aacagcacaa cagagcgcgct caatgtcttg     120 ctcattattg ttgatgatct tagacccagc ttggggtgct acggggataa actcgtaagg     180
tcaccgaaca ttgatcagct ggcatcacat tcccttctct tccaaaatgc gtttgcgcag     240
caagccgtat gcgcaccaag tagggtttct ttccttacgg gccgacggcc agatacgaca     300
cggctctacg actttaattc ctactggcgc gtacacgcag ggaactttag cacgatcccc     360
cagtatttta aggagaacgg ttacgtcaca atgagcgttg ggaaagtttt tcaccctggg     420
attagtagca accatacaga cgacagtccc tactcatggt cattcccacc ttaccatcct     480
agcagcgaaa aatacgaaaa caccaaaact tgccgcggac ctgatggaga acttcatgcc     540
aacctcctct gccccgttga cgtactcgac gtccctgagg gcactctccc cgacaaacaa     600
agcacagaac aggcgattca gctcctggaa aaaatgaaaa cgtccgcatc accattttt     660 ttggctgttg gttaccataa gcctcatatc ccttttagat atcccaaaga atttcagaaa     720
ctctacccac ttgagaatat aactttggcg ccagatccag aggtgccaga tggtctgccc     780
cctgttgctt acaacccctg gatggatatt cgacaaaggg aagacgtcca agcgctcaac     840

-continued

```
atctctgttc cctatggtcc gataccagtt gacttccaaa gaaagatacg ccaatcatac      900
tttgcgagtg tcagttatct cgatacccaa gtaggtaggc tgctgagtgc cctcgacgac      960
ctccagctgg ctaacagtac catcatagct tttaccagcg accacggctg ggctctgggg     1020
gagcacgggg agtgggccaa atatagcaac tttgacgtgg ctactcacgt accacttata     1080
ttttacgtac cgggtcgcac ggcctctctt cccgaagccg gggaaaagct tttcccttac     1140
ctcgacccct tcgattccgc gtcacaactg atggagccag gaagacgag catggacctg      1200 gtcgaactgg tgagcctgtt ccctacactc gcagggctgg cagggctgca ggtccctcca     1260
cgctgcccag tccctagctt tcatgttgaa ctctgtagag agggtaaaaa cctgctcaag     1320
catttcaggt tccgcgatct tgaggaagat ccctatctcc ctggaaaccc gcgagaactg     1380
attgcatata gtcagtatcc acgcccaagt gacatccccc agtggaactc agacaaacca     1440
agccttaagg atattaaaat tatgggctat tcaattagga caatagacta tcggtacacc     1500
gtgtgggtcg ggtttaatcc tgacgagttc ttggcaaact tcagtgatat ccatgctggc     1560
gaactttatt tcgtggattc agatcccctc caagaccaca atatgtataa cgatagccaa     1620
ggaggagacc tgtttcagct gctcatgcct tga                                  1653
```

<210> SEQ ID NO 2
<211> LENGTH: 1653
<212> TYPE: DNA
<213> ORGANISM: Homo sapiens

<400> SEQUENCE: 2

```
atgccgccac cccggaccgg ccgaggcctt ctctggctgg gtctggttct gagctccgtc       60
tgcgtcgccc tcggatccga aacgcaggcc aactcgacca cagatgctct gaacgttctt      120
ctcatcatcg tggatgacct gcgcccctcc ctgggctgtt atgggggataa gctggtgagg     180 tccccaaata ttgaccaact ggcatcccac agcctcctct ccagaatgc ctttgcgcag       240 caagcagtgt gcgccccgag ccgcgtttct ttcctcactg gcaggagacc tgacaccacc      300
cgcctgtacg acttcaactc ctactggagg gtgcacgctg aaacttctc caccatcccc       360 cagtacttca aggagaatgg ctatgtgacc atgtcggtgg gaaaagtctt tcaccctggg      420
atatcttcta accataccga tgattctccg tatagctggt cttttccacc ttatcatcct       480
tcctctgaga agtatgaaaa cactaagaca tgtcgagggc cagatggaga actccatgcc      540
aacctgcttt gccctgtgga tgtgctggat gttcccgagg gcaccttgcc tgacaaacag      600
agcactgagc aagccataca gttgttggaa aagatgaaaa cgtcagccag tcctttcttc      660
ctggccgttg ggtatcataa gccacacatc cccttcagat accccaagga atttcagaag      720
ttgtatccct tggagaacat caccctggcc ccgatcccg aggtccctga tggcctaccc       780
cctgtggcct acaacccctg gatggacatc aggcaacggg aagacgtcca agccttaaac      840
atcagtgtgc cgtatggtcc aattcctgtg gactttcagc ggaaaatccg ccagagctac      900
tttgcctctg tgtcatattt ggatacacag gtcggccgcc tcttgagtgc tttggacgat      960
cttcagctgg ccaacagcac catcattgca tttacctcgg atcatgggtg ggctctaggt     1020
gaacatggag aatgggccaa atacagcaat tttgatgttg ctacccatgt tcccctgata     1080
ttctatgttc ctggaaggac ggcttcactt ccggaggcag gcgagaagct tttcccttac     1140
ctcgacccct ttgattccgc ctcacagttg atggagccag gcaggcaatc catggacctt      1200
gtggaacttg tgtctctttt tcccacgctg gctggacttg caggactgca ggttccacct     1260
```

-continued

```
cgctgccccg ttccttcatt tcacgttgag ctgtgcagag aaggcaagaa ccttctgaag    1320
cattttcgat tccgtgactt ggaagaggat ccgtacctcc ctggtaatcc ccgtgaactg    1380
attgcctata gccagtatcc ccggccttca gacatccctc agtggaattc tgacaagccg    1440
agtttaaaag atataaagat catgggctat tccatacgca ccatagacta taggtatact    1500
gtgtgggttg gcttcaatcc tgatgaattt ctagctaact tttctgacat ccatgcaggg    1560
gaactgtatt ttgtggattc tgacccattg caggatcaca atatgtataa tgattcccaa    1620
ggtggagatc ttttccagtt gttgatgcct tga                                 1653
```

<210> SEQ ID NO 3
<211> LENGTH: 2354
<212> TYPE: DNA
<213> ORGANISM: Artificial sequence
<220> FEATURE:
<223> OTHER INFORMATION: Synthetic polynucleotide

<400> SEQUENCE: 3

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggggtt taaacctaaa     120
aaacctccca cacctccccc tgaacctgaa acataaaatg aatgcaattg ttgttgttaa     180
cttgtttatt gcagcttata atggttacaa ataaagcaat agcatcacaa atttcacaaa     240
taaagcattt ttttcactgc attctagttg tggtttgtcc aaactcatca atgtatctta     300
tcatgtctga gatcttcagg gcataagaag ttgaaacaaa tccccgccct ggctatcgtt     360
gtacatgtta tgatcttgca agggatcgct atctacgaaa tacaactctc cagcgtgaat     420
gtcgctaaag ttagccaaaa actcatctgg gttaaaacct acccagacag tatagcggta     480
atcaatcgtc cgtatggaat atcccatgat tttaatatct ttaagtgatg gtttatcgga     540
gttccattgt ggaatatcgg atggccttgg atactgtgaa taagcaataa gctctcgcgg     600
attacctggc aggtatgggt cctcctcaag gtccctaaac cgaaagtgtt tcaacaaatt     660
ctttccctct cggcacagtt ctacatggaa agacggcaca ggacatctag gtgggacctg     720
caatccggcg agccccgcca gagttgggaa aagggatacc agctcaacaa ggtccataga     780
ttgtcgtcca ggctccatga gctggcttgc ggaatcaaat gggtcgaggt acggaaacag     840
tttttcaccg gcttctggca aagaagccgt ccgcccaggc acataaaata tcagagggac     900
gtgcgtggcg acgtcaaaat tagaatattt tgcccattca ccatgctctc cgagtgccca     960
gccgtgatcg gacgtaaaag ctatgatagt gctattagcc aactggagat cgtccaatgc    1020
actcaaaagc cttccgacct gagtgtcaag gtagcttaca gacgcgaagt agctttgtcg    1080
gatttttctc tggaaatcta ctggaatcgg gccataagga cactgatgt tgagagcttg     1140 gacatcttcc ctttgcctaa tgtccatcca aggattatac gccaccggcg gcagcccatc    1200
ggggacctcc gggtccggag cgagcgtgat attttcaaga ggatagagtt tctggaattc    1260
tttcgggtat ctaaagggaa tatgcggttt gtggtagccg acggcaggaa aaaagggga     1320 ggcgctggtc ttcatcttct cgagcaactg aatggcctgt tcggtgcttt gcttgtcagg    1380
cagtgtccct tctggaacgt caagtacgtc gacagggcaa agcaaattcg catgcaactc    1440
tccatcgggc ccgcgacaag tctttgtatt ttcgtatttt tcgctactcg gatggtaagg    1500
agggaagctc catgagtacg ggctgtcgtc cgtgtgattg gaactaattc caggatgaaa    1560 taccttttccc acgctcatag tcacgtaccc gttttctttg aagtactggg gaatcgtaga    1620
gaaattcccc gcatgaaccc gccaatagga attaaaatcg taaagtcgcg tggtgtctgg    1680
```

-continued

```
tcgccgccca gtcagaaatg agactcgtga tggcgcgcaa actgcttgct gagcgaaagc    1740
attttgaaaa aggagggaat gtgacgcgag ctgatcgatg ttgggggatc ttaccagctt    1800
atctccgtag cagcccaggc tagggcgcaa gtcatctaca attatcagca atacattgag    1860
cgcatccgtg gtgctattcg cctgggtctc ggacccgagg gcaacacaaa cggatgacag    1920
aaccaatccc aaccacagca agcccgtcc agtccgtggt ggaggcatga tggggcgacc     1980
ggtcgagcgg ttcactaaac gagctctgct tatatagacc tcccaccgta cacgcctacc    2040
gcccatttgc gtcaatgggg cggagttgtt acgacatttt ggaaagtccc gttgattttg    2100
gtgccaaaac aaactcccat tgacgtcaat ggggtggaga cttggaaatc cccgtgagtc    2160 cggggggtcgt tgggcggtca gccaggcggg ccatttaccg taagttatgt aacgaaagct   2220
tcctaggaac ccctagtgat ggagttggcc actccctctc tgcgcgctcg ctcgctcact    2280
gaggccgggc gaccaaaggt cgcccgacgc ccgggctttg cccgggcggc ctcagtgagc    2340
gagcgagcgc gcag                                                      2354
```

<210> SEQ ID NO 4
<211> LENGTH: 5948
<212> TYPE: DNA
<213> ORGANISM: Artificial sequence
<220> FEATURE:
<223> OTHER INFORMATION: Synthetic polynucleotide

<400> SEQUENCE: 4

```
cagcagctgc gcgctcgctc gctcactgag gccgccgggg caaagcccgg gcgtcgggcg      60
acctttggtc gcccggcctc agtgagcgag cgagcgcgca gagagggagt ggggtttaaa     120
cctaaaaaac ctcccacacc tccccctgaa cctgaaacat aaaatgaatg caattgttgt     180
tgttaacttg tttattgcag cttataatgg ttacaaataa agcaatagca tcacaaattt     240
cacaaataaa gcattttttt cactgcattc tagttgtggt ttgtccaaac tcatcaatgt     300
atcttatcat gtctgagatc ttcagggcat aagaagttga aacaaatccc cgccctggct     360
atcgttgtac atgttatgat cttgcaaggg atcgctatct acgaaataca actctccagc     420
gtgaatgtcg ctaaagttag ccaaaaactc atctgggtta aaacctaccc agacagtata     480
gcggtaatca atcgtccgta tggaatatcc catgatttta atatctttaa gtgatggttt     540
atcggagttc cattgtggaa tatcggatgg ccttggatac tgtgaataag caataagctc     600
tcgcggatta cctggcaggt atgggtcctc ctcaaggtcc ctaaaccgaa agtgtttcaa     660
caaattcttt ccctctcggc acagttctac atggaaagac ggcacaggac atctaggtgg     720
gacctgcaat ccggcgagcc ccgccagagt tgggaaaagg gataccagct caacaaggtc     780
catagattgt cgtccaggct ccatgagctg gcttgcggaa tcaaatgggt cgaggtacgg     840
aaacagtttt tcaccggctt ctggcaaaga agccgtccgc ccaggcacat aaaatatcag     900
agggacgtgc gtggcgacgt caaaattaga atattttgcc cattcaccat gctctccgag     960
tgcccagccg tgatcggacg taaaagctat gatagtgcta ttagccaact ggagatcgtc    1020
caatgcactc aaaagccttc cgacctgagt gtcaaggtag cttacagacg cgaagtagct    1080
ttgtcggatt tttctctgga aatctactgg aatcgggcca taggaacac tgatgttgag     1140 agcttggaca tcttcccttt gcctaatgtc catccaagga ttatacgcca ccggcggcag    1200
cccatcgggg acctccgggt ccggagcgag cgtgatattt tcaagaggat agagtttctg    1260
gaattctttc gggtatctaa agggaatatg cggtttgtgg tagccgacgg ccaggaaaaa    1320
```

-continued

```
aggggaggcg ctggtcttca tcttctcgag caactgaatg gcctgttcgg tgctttgctt   1380
gtcaggcagt gtcccttctg gaacgtcaag tacgtcgaca gggcaaagca aattcgcatg   1440
caactctcca tcgggcccgc gacaagtctt tgtattttcg tattttttcgc tactcggatg   1500 gtaaggaggg aagctccatg agtacgggct gtcgtccgtg tgattggaac taattccagg   1560
atgaaatacc tttcccacgc tcatagtcac gtacccgttt tctttgaagt actggggaat   1620
cgtagagaaa ttccccgcat gaacccgcca ataggaatta aaatcgtaaa gtcgcgtggt   1680
gtctggtcgc cgcccagtca gaaatgagac tcgtgatggc gcgcaaactg cttgctgagc   1740
gaaagcattt tgaaaaagga gggaatgtga cgcgagctga tcgatgttgg gggatcttac   1800
cagcttatct ccgtagcagc ccaggctagg gcgcaagtca tctacaatta tcagcaatac   1860
attgagcgca tccgtggtgc tattcgcctg ggtctcggac ccgagggcaa cacaaacgga   1920
tgacagaacc aatcccaacc acagcaagcc ccgtccagtc cgtggtggag gcatgatggg   1980
gcgaccggtc gagcggttca ctaaacgagc tctgcttata tagacctccc accgtacacg   2040
cctaccgccc atttgcgtca atggggcgga gttgttacga cattttggaa agtcccgttg   2100
attttggtgc caaaacaaac tcccattgac gtcaatgggg tggagacttg gaaatccccg   2160
tgagtccggg ggtcgttggg cggtcagcca ggcgggccat ttaccgtaag ttatgtaacg   2220
aaagcttcct aggaacccct agtgatggag ttggccactc cctctctgcg cgctcgctcg   2280
ctcactgagg ccgggcgacc aaaggtcgcc cgacgcccgg gctttgcccg gcggcctca   2340 gtgagcgagc gagcgcgcag ctggcgtaat agcgaagagg cccgcaccga tcgcccttcc   2400
caacagttgc gcagcctgaa tggcgaatgg cgattccgtt gcaatggctg gcggtaatat   2460
tgttctggat attaccagca aggccgatag tttgagttct tctactcagg caagtgatgt   2520
tattactaat caaagaagta ttgcgacaac ggttaatttg cgtgatggac agactctttt   2580
actcggtggc ctcactgatt ataaaaacac ttctcaggat tctggcgtac cgttcctgtc   2640
taaaatccct ttaatcggcc tcctgtttag ctcccgctct gattctaacg aggaaagcac   2700
gttatacgtg ctcgtcaaag caaccatagt acgcgccctg tagcggcgca ttaagcgcgg   2760
cgggtgtggt ggttacgcgc agcgtgaccg ctacacttgc cagcgcccta gcgcccgctc   2820
ctttcgcttt cttcccttcc tttctcgcca cgttcgccgg ctttccccgt caagctctaa   2880
atcgggggct ccctttaggg ttccgattta gtgctttacg gcacctcgac cccaaaaaac   2940
ttgattaggg tgatggttca cgtagtgggc catcgccctg atagacggtt tttcgccctt   3000
tgacgttgga gtccacgttc tttaatagtg gactcttgtt ccaaactgga acaacactca   3060
accctatctc ggtctattct tttgatttat aagggatttt gccgatttcg gcctattggt   3120
taaaaaatga gctgatttaa caaaaattta acgcgaattt taacaaaata ttaacgctta   3180
caatttaaat atttgcttat acaatcttcc tgtttttggg gcttttctga ttatcaaccg   3240
gggtacatat gattgacatg ctagttttac gattaccgtt catcgattct cttgtttgct   3300
ccagactctc aggcaatgac ctgatagcct ttgtagagac ctctcaaaaa tagctaccct   3360
ctccggcatg aatttatcag ctagaacggt tgaatatcat attgatggtg atttgactgt   3420
ctccggcctt tctcacccgt ttgaatcttt acctacacat tactcaggca ttgcatttaa   3480
aatatatgag ggttctaaaa attttttatcc ttgcgttgaa ataaaggctt ctcccgcaaa   3540
agtattacag ggtcataatg tttttggtac aaccgattta gctttatgct ctgaggcttt   3600
attgcttaat tttgctaatt ctttgccttg cctgtatgat ttattggatg ttggaatcgc   3660
ctgatgcggt attttctcct tacgcatctg tgcggtattt cacaccgcat atggtgcact   3720
```

```
ctcagtacaa tctgctctga tgccgcatag ttaagccagc cccgacaccc gccaacaccc      3780
gctgacgcgc cctgacgggc ttgtctgctc ccggcatccg cttacagaca agctgtgacc      3840
gtctccggga gctgcatgtg tcagaggttt tcaccgtcat caccgaaacg cgcgagacga      3900
aagggcctcg tgatacgcct attttttatag gttaatgtca tgataataat ggtttcttag      3960
acgtcaggtg gcacttttcg gggaaatgtg cgcggaaccc ctatttgttt attttttctaa      4020 atacattcaa atatgtatcc gctcatgaga caataaccct gataaatgct tcaataatat      4080
tgaaaaagga agagtatgag tattcaacat ttccgtgtcg cccttattcc cttttttgcg      4140
gcattttgcc ttcctgtttt tgctcaccca gaaacgctgg tgaaagtaaa agatgctgaa      4200
gatcagttgg gtgcacgagt gggttacatc gaactggatc tcaacagcgg taagatcctt      4260
gagagttttc gccccgaaga acgttttcca atgatgagca cttttaaagt tctgctatgt      4320
ggcgcggtat tatcccgtat tgacgccggg caagagcaac tcggtcgccg catacactat      4380
tctcagaatg acttggttga gtactcacca gtcacagaaa agcatcttac ggatggcatg      4440
acagtaagag aattatgcag tgctgccata accatgagtg ataacactgc ggccaactta      4500
cttctgacaa cgatcggagg accgaaggag ctaaccgctt ttttgcacaa catgggggat      4560
catgtaactc gccttgatcg ttgggaaccg gagctgaatg aagccatacc aaacgacgag      4620
cgtgacacca cgatgcctgt agcaatggca caacgttgc gcaaactatt aactggcgaa      4680
ctacttactc tagcttcccg gcaacaatta atagactgga tggaggcgga taaagttgca      4740
ggaccacttc tgcgctcggc ccttccggct ggctggttta ttgctgataa atctggagcc      4800
ggtgagcgtg ggtctcgcgg tatcattgca gcactggggc cagatggtaa gccctcccgt      4860
atcgtagtta tctacacgac ggggagtcag gcaactatgg atgaacgaaa tagacagatc      4920
gctgagatag gtgcctcact gattaagcat tggtaactgt cagaccaagt ttactcatat      4980
atactttaga ttgatttaaa acttcatttt taatttaaaa ggatctaggt gaagatcctt      5040
tttgataatc tcatgaccaa aatcccttaa cgtgagtttt cgttccactg agcgtcagac      5100
cccgtagaaa agatcaaagg atcttcttga tcctttttt ttctgcgcgt aatctgctgc      5160
ttgcaaacaa aaaaaccacc gctaccagcg gtggtttgtt tgccggatca agagctacca      5220 actcttttc cgaaggtaac tggcttcagc agagcgcaga taccaaatac tgttcttcta      5280
gtgtagccgt agttaggcca ccacttcaag aactctgtag caccgcctac atacctcgct      5340
ctgctaatcc tgttaccagt ggctgctgcc agtggcgata agtcgtgtct taccgggttg      5400
gactcaagac gatagttacc ggataaggcg cagcggtcgg gctgaacggg gggttcgtgc      5460
acacagccca gcttggagcg aacgacctac accgaactga gatacctaca gcgtgagcta      5520
tgagaaagcg ccacgcttcc cgaagggaga aaggcggaca ggtatccggt aagcggcagg      5580
gtcggaacag gagagcgcac gagggagctt ccagggggaa acgcctggta tctttatagt      5640
cctgtcgggt ttcgccacct ctgacttgag cgtcgatttt tgtgatgctc gtcaggggg      5700 cggagcctat ggaaaaacgc cagcaacgcg gcctttttac ggttcctggc cttttgctgg      5760 cctttttgctc acatgttctt tcctgcgtta tcccctgatt ctgtggataa ccgtattacc      5820
gcctttgagt gagctgatac cgctcgccgc agccgaacga ccgagcgcag cgagtcagtg      5880
agcgaggaag cggaagagcg cccaatacgc aaaccgcctc tccccgcgcg ttggccgatt      5940
cattaatg                                                                5948
```

-continued

```
<210> SEQ ID NO 5
<211> LENGTH: 1653
<212> TYPE: DNA
<213> ORGANISM: Artificial sequence
<220> FEATURE:
<223> OTHER INFORMATION: Synthetic polynucleotide

<400> SEQUENCE: 5
atgcctcccc ctaggacggg tcggggcctc ttgtggctgg gcctggtact gagttcagtg      60
tgcgtagcac tggggagcga gacacaggcc aacagcacca cggacgcgct taacgtattg     120
ctcattattg ttgatgatct cgccctagt ctgggttgct acggtgacaa acttgttagg      180
tcacctaaca tagaccagct ggctagtcac agccttcttt ttcaaaatgc ctttgctcaa     240
caagctgtat gcgcccctag tcgcgtgagt ttccttactg gtcgacgacc cgatacaaca     300
cgcctttatg actttaacag ttactggcgc gtccatgcag gcaacttctc aacgataccg     360
cagtacttca aggaaaacgg ctacgtgacc atgtctgttg gcaaggtatt tcatcctggt     420
atttcaagca accatacaga cgattctcca tactcttggt catttccccc atatcacccg     480
agctctgaga aatacgaaaa cacaaaaaca tgtagaggac cggacggtga gctgcacgca     540
aatttgcttt gcccggtcga cgtactcgat gtcccggagg ggactcttcc tgataagcaa     600
agcaccgaac aggcaatcca gctgctcgaa aaaatgaaga ctagcgcttc accatttttt     660
ctcgctgtgg gctatcacaa accacacatc ccttttcgat atcctaaaga gtttcaaaaa     720
ctctaccctc tcgaaaacat tactttggcc cccgatcccg aggtcccgga cggactgcca     780
cccgtcgcgt acaatccctg gatggacatc cggcaacgag aagacgtgca agcactgaat     840
atttccgtgc cctacgggcc aattcctgtt gattttcaaa ggaaaatacg gcagagttat     900
tttgcgtccg tctcatacct tgacacgcag gtaggaaggc tcctttcagc tttggacgat     960
ttgcaactgg caaattcaac aattatagca ttcacttcag accacgggtg ggcgctcggt    1020
gaacacgggg agtgggctaa gtactccaac tttgacgtgg cgacacatgt accgcttata    1080
ttttacgtcc ctggtagaac tgcgagcctc ccagaggccg gagagaagct cttcccatac    1140
ctcgatcctt ttgattctgc aagtcagttg atggagcccg gacgacaaag tatggacctt    1200
gttgagctcg tatctctgtt tccaacgctt gctgggctgg cagggctgca agttcctcct    1260
aggtgtccgg ttccttcctt ccatgttgag ctctgcagag aagggaaaaa cctcctcaaa    1320
catttccgat tcagggacct ggaggaagat ccctacttgc cagggaatcc acgagagctg    1380
atagcctact cacagtatcc acggcccagt gatatccccc aatggaacag tgataagccc    1440
tccctgaaag atatcaagat aatgggctat agcattagaa caatcgacta caggtatacc    1500
gtttgggtcg gttttaatcc cgatgaattc ctggcgaact tcagtgatat ccacgcagga    1560
gagctgtact tcgttgactc cgatccattg caggatcaca acatgtataa tgatagtcag    1620
ggcggtgatc tttttcagct gcttatgcct tga                                 1653

<210> SEQ ID NO 6
<211> LENGTH: 1653
<212> TYPE: DNA
<213> ORGANISM: Artificial sequence
<220> FEATURE:
<223> OTHER INFORMATION: Synthetic polynucleotide

<400> SEQUENCE: 6
atgcctccgc ctcggacagg acggggactg ctctggcttg ggctggtgct tagcagcgtc      60
```

-continued

```
tgtgtcgctc tgggctcaga aacccaggcg aattcaacga cagacgccct gaacgtcttg      120
cttattatag tggacgatct gcgaccatca ttggggtgtt atggggataa gttggtgcga      180
tctcccaaca ttgaccaact ggcttctcac agcctccttt tccaaaacgc tttcgcgcag      240
caagcggtct gcgctccttc aagagtaagc tttctcacag gaagacgccc cgacaccaca      300
cgcttgtacg attttaactc atattggaga gttcatgcgg ggaacttttc aaccatccca      360
cagtatttta aggagaatgg ctacgtcacg atgagtgtgg gaaaagtatt ccatccgggc      420
atttccagca atcataccga tgatagccct tatagttggt ccttcccgcc ctaccacccg      480
agttccgaga agtatgaaaa tactaaaaca tgccgaggcc ccgacggtga attgcatgcc      540
aacttgctct gccccgtcga tgtacttgac gtacctgagg gtacactccc cgataagcag      600
tctacggaac aagccataca actgctggaa aaaatgaaga catcagctag tccgttcttc      660
ttggcagttg gttaccataa gccccatata ccatttcggt atccaaagga atttcaaaag      720
ttgtatccac tggagaatat aaccctcgcc cctgacccgg aggtcccaga cggtctcccc      780
ccagttgctt acaacccctg gatggatatt aggcagcgag aagacgtaca ggctttgaat      840
atctccgtac catacggacc gattcccgta gatttccagc gaaaaatccg ccagtcctac      900
tttgcgtccg tatcatacct ggacactcaa gttggcagat tgctttccgc attggatgat      960
ctgcagttgg cgaatagcac catcattgct ttcactagcg atcacggatg ggccctggga     1020
gagcatggtg agtgggcgaa gtatagcaac ttcgacgtcg caacgcacgt gcctctcatt     1080
ttttacgttc ctgggcgaac ggcttctttg cctgaagcag gggagaagct cttcccatat     1140
ctggacccct tcgatagcgc ttctcaattg atggaaccag gacggcagag catggatctc     1200
gtagaactgg tctcactttt cccgaccctc gcgggtcttg caggactcca ggtccctcct     1260
cggtgccctg tacctagttt tcacgtggag ctgtgtaggg aggggaagaa cttgctcaaa     1320
cattttaggt tccgggacct tgaggaagat ccgtatctgc caggtaatcc cagagagctt     1380
atcgcttata gtcagtaccc acggccgagc gacattcccc agtggaatag tgataagccc     1440
agcttgaagg acattaagat aatgggatac agcattcgga ctatagacta tcggtacact     1500
gtctgggtcg gttttaaccc agatgaattt ttggctaatt tttcagacat ccatgctggg     1560
gagctttatt ttgtagatag tgatcctttg caagatcata atatgtataa cgacagccaa     1620
ggtggagact tgttccaatt gcttatgcca tga                                  1653
```

<210> SEQ ID NO 7
<211> LENGTH: 1653
<212> TYPE: DNA
<213> ORGANISM: Artificial sequence
<220> FEATURE:
<223> OTHER INFORMATION: Synthetic polynucleotide

<400> SEQUENCE: 7

```
atgccaccgc caagaacggg cagggggtctt ctgtggctgg gtcttgtttt gagtagtgtc       60
tgtgtggccc tcggtagtga gacccaggct aacagcacaa cagacgcgct caatgtcttg      120
ctcattattg ttgatgatct tagacccagc ttggggtgct acgggataa actcgtaagg      180 tcaccgaaca ttgatcagct ggcatcacat tcccttctct tccaaaatgc gtttgcgcag      240
caagccgtat gcgcaccaag tagggtttct ttccttacgg gccgacggcc agatacgaca      300
cggctctacg actttaattc ctactggcgc gtacacgcag ggaactttag cacgatcccc      360
cagtatttta aggagaacgg ttacgtcaca atgagcgttg ggaaagtttt tcaccctggg      420
attagtagca accatacaga cgacagtccc tactcatggt cattcccacc ttaccatcct      480
```

-continued

```
agcagcgaaa aatacgaaaa caccaaaact tgccgcggac ctgatggaga acttcatgcc      540
aacctcctct gccccgttga cgtactcgac gtccctgagg gcactctccc cgacaaacaa      600
agcacagaac aggcgattca gctcctggaa aaaatgaaaa cgtccgcatc accatttttt      660
ttggctgttg gttaccataa gcctcatatc ccttttagat atcccaaaga atttcagaaa      720
ctctacccac ttgagaatat aactttggcg ccagatccag aggtgccaga tggtctgccc      780
cctgttgctt acaacccctg gatggatatt cgacaaaggg aagacgtcca agcgctcaac      840
atctctgttc cctatggtcc gataccagtt gacttccaaa gaaagatacg ccaatcatac      900
tttgcgagtg tcagttatct cgatacccaa gtaggtaggc tgctgagtgc cctcgacgac      960
ctccagctgg ctaacagtac catcatagct tttaccagcg accacggctg ggctctgggg     1020
gagcacgggg agtgggccaa atatagcaac tttgacgtgg ctactcacgt accacttata     1080
ttttacgtac cgggtcgcac ggcctctctt cccgaagccg gggaaaagct tttcccttac     1140
ctcgacccct tcgattccgc gtcacaactg atggagccag gaagacagag catggacctg     1200
gtcgaactgg tgagcctgtt ccctacactc gcagggctgg cagggctgca ggtccctcca     1260
cgctgcccag tccctagctt tcatgttgaa ctctgtagag agggtaaaaa cctgctcaag     1320
catttcaggt tccgcgatct tgaggaagat ccctatctcc ctggaaaccc gcgagaactg     1380
attgcatata gtcagtatcc acgcccaagt gacatccccc agtggaactc agacaaacca     1440
agccttaagg atattaaaat tatgggctat tcaattagga caatagacta tcggtacacc     1500
gtgtgggtcg ggtttaatcc tgacgagttc ttggcaaact tcagtgatat ccatgctggc     1560
gaactttatt tcgtggattc agatcccctc caagaccaca atatgtataa cgatagccaa     1620
ggaggagacc tgtttcagct gctcatgcct tga                                  1653
```